United States Patent
Melander et al.

(10) Patent No.: US 9,439,436 B2
(45) Date of Patent: *Sep. 13, 2016

(54) USE OF ARYL CARBAMATES IN AGRICULTURE AND OTHER PLANT-RELATED AREAS

(71) Applicant: North Carolina State University, Raleigh, NC (US)

(72) Inventors: Christian Melander, Raleigh, NC (US); Steven A. Rogers, Lawrence, KS (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,480

(22) Filed: Jul. 30, 2015

(65) Prior Publication Data
US 2015/0327552 A1    Nov. 19, 2015

Related U.S. Application Data

(63) Continuation of application No. 13/778,425, filed on Feb. 27, 2013, now Pat. No. 9,125,408, which is a continuation of application No. PCT/US2011/050005, filed on Aug. 31, 2011.

(60) Provisional application No. 61/378,989, filed on Sep. 1, 2010.

(51) Int. Cl.
| | |
|---|---|
| *A01N 47/18* | (2006.01) |
| *A01N 47/12* | (2006.01) |
| *A01N 59/20* | (2006.01) |
| *A01N 63/00* | (2006.01) |
| *C07C 271/34* | (2006.01) |
| *C07D 213/40* | (2006.01) |
| *C07D 209/14* | (2006.01) |
| *A01N 47/16* | (2006.01) |

(52) U.S. Cl.
CPC ............... *A01N 47/12* (2013.01); *A01N 47/16* (2013.01); *A01N 47/18* (2013.01); *A01N 59/20* (2013.01); *A01N 63/00* (2013.01); *C07C 271/34* (2013.01); *C07D 209/14* (2013.01); *C07D 213/40* (2013.01); *C07C 2101/14* (2013.01)

(58) Field of Classification Search
CPC ...... A01N 47/12; A01N 47/16; A01N 59/20; C07C 2101/14; C07C 271/34
USPC ................. 424/93.6, 630, 633; 514/357, 415
See application file for complete search history.

(56) References Cited

U.S. PATENT DOCUMENTS

| 4,373,105 A | 2/1983 | Rohr et al. |
| 5,411,967 A | 5/1995 | Kao et al. |
| 6,239,175 B1 | 5/2001 | Hinks et al. |
| 7,074,742 B2 | 7/2006 | Neubert et al. |
| 7,291,641 B2 | 11/2007 | Chabrier De Lassauniere et al. |
| 8,884,022 B2 | 11/2014 | Melander et al. |
| 2004/0072880 A1 | 4/2004 | Lloyd et al. |
| 2007/0014739 A1 | 1/2007 | Eldridge et al. |
| 2007/0276010 A1 | 11/2007 | Benbow et al. |
| 2009/0203647 A1 | 8/2009 | Benko et al. |

FOREIGN PATENT DOCUMENTS

| EP | 0017411 | 10/1980 |
| JP | 11035545 | 2/1999 |
| WO | WO 2009/144179 A1 | 12/2009 |

OTHER PUBLICATIONS

Aridogan BC et al. Antimicrobial Activity and Chemical Composition of Some Essential Oils. Arch. Pharm. Res. 2002; 25(6), 860-864.
Banker, G.S. et al. "Modern Pharmaceutics, 3ed.", Marcel Dekker, New York, 1996, pp. 451 and 596.
Ben Afra A et al. Antimicrobial activity of carvacrol related to its chemical structure. Lett. Appl. Microbiol. 2006; 43, 149-154.
Filoche SK et al. Antimicrobial effects of essential oils in combination with chlorhexidine digluconate. Oral Microb. Immun. 2005; 20, 221-225.
Giorgio: Chirality, 2007, 19, 434-445.
International Search Report and Written Opinion, PCT/US2011/042941, mailed Nov. 18, 2011.
Iscan G et al. Antimicrobial Screening of *Mentha piperita* Essential Oils. J. Agric. Food Chem. 2002; 50, 3943-3946.
Kurita N and Koike S. Synergistic Antimicrobial Effect of Sodium Chloride and Essential Oil Components. Agric. Biol. Chem. 1982; 46(1), 159-165.
Rogers SA et al. Synthesis and biological evaluation of 2-aminoimadazole/carbamate hybrid anti-biofilm and anti-microbial agents. Bioorganic and Medicinal Chemistry Letters. 2011; 1257-1260.
Rogers SA et al. Synthesis and bacterial biofilm inhibition studies of ethyl N-(2-phenethyl) carbamate derivatives. Organic and Biomolecular Chemistry. 2010; 8, 3857-3859.
Schelz Z et al. Antimicrobial and antiplasmid activities of essential oils. Fitoterapia. 2006; 77(4), 279-285.

(Continued)

*Primary Examiner* — Johann R Richter
*Assistant Examiner* — Yanzhi Zhang
(74) *Attorney, Agent, or Firm* — Myers Bigel & Sibley, P.A.

(57) ABSTRACT

Disclosure is provided for methods of preventing, removing or inhibiting microbial biofilm formation or microbial infection in a plant or plant part thereof, including applying thereto a treatment effective amount of an aryl carbamate as described herein, or an agriculturally acceptable salt thereof. Methods of enhancing a microbicide (e.g., including a copper, antibiotic, bacteriophage, etc.) and/or plant defense activator are also provided, including applying an active compound as described herein. Compositions comprising an aryl carbamate compound as described herein in an agriculturally acceptable carrier are also provided, and in some embodiments the compositions further include a microbicide (e.g., including copper, antibiotic, bacteriophage, etc.) and/or a plant defense activator.

29 Claims, No Drawings

(56) References Cited

OTHER PUBLICATIONS

Sivropoulou A et al. Antimicrobial and Cytotoxic Activities of *Origanum* Essential Oils. J. Agric. Food Chem. 1996; 44, 1202-1205.

Tsuji: Tetrahedron: Asymmetry, 2003, 14, 177-180.

Ultee A et al. Antimicrobial Activity of Carvacrol toward *Bacillus cereus* on Rice. J. Food Protect. 2000; 63(5), 620-624.

Wermuth: Practice of Medicinal Chemistry, Third edition, 2008, Elsevier, pp. 126, 298, 401-403, 431.

Wolff, Manfred E. "Burger's Medicinal Chemistry, 5ed., Part I", John Wiley & Sons, 1995, pp. 975-977.

Yamada A et al. Development of Chemical Substances Regulating Biofilm Formation. Bull. Chem. Soc. Jpn. 1997; 70, 3061-3069.

USE OF ARYL CARBAMATES IN AGRICULTURE AND OTHER PLANT-RELATED AREAS

RELATED APPLICATIONS

This application is a continuation of and claims priority to U.S. patent application Ser. No. 13/778,425, filed Feb. 27, 2013, now allowed, which is a continuation of PCT/US2011/050005, filed Aug. 31, 2011, which claims the benefit under 35 U.S.C. §119(e) to U.S. Provisional Patent Application No. 61/378,989, filed Sep. 1, 2010, the contents of each of which is incorporated by reference herein in its entirety.

FIELD

This disclosure relates to compounds, compositions and methods useful for controlling biofilms and microorganisms in agriculture and/or environments where plants may grow.

BACKGROUND

New approaches are urgently needed to improve agricultural production, given the steadily growing global population that is predicted to reach 6-9 billion persons by mid-century, the continual strain on existing and finite agricultural lands, and the recent diversion of valuable agricultural land from production of crops to production of biomass for fuels. Here we describe new approaches to increase agricultural production by controlling the adverse effects of microorganisms on plants.

The five main crops on which modern societies depend most heavily include corn, cotton, rice, soybeans, and wheat. All of these crops are affected in a deleterious manner by biofilm formation. In addition, other valuable plants such as those producing fruits and vegetables are similarly affected. Plants grown for biomass stand to increase as a valuable crop, albeit not for food, and also can benefit from protection from biofilm formation. Forestry crops, turfgrass, and ornamentals, and aquatic sites, also suffer from biofilms.

SUMMARY

The present disclosure relates to a method of preventing, removing or inhibiting microbial biofilm formation or microbial infection in a plant or plant part thereof, comprising applying to the plant or plant part, or environment where plants may grow, a treatment effective amount of a compound of Formula (I):

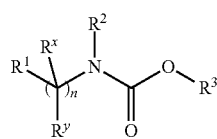

wherein:
R$^1$ is an aryl, an amine-substituted aryl, or a heteroaryl having at least one nitrogen atom;
n=0 to 10, saturated or unsaturated;
each occurrence of R$^x$ and R$^y$ is present or absent (depending upon chain saturation), and is each independently H or alkyl;
R$^2$ is selected from the group consisting of: H, alkyl, alkenyl and alkynyl; and R$^3$ is alkyl, substituted cycloalkyl or unsubstituted cycloalkyl,
or an agriculturally acceptable salt thereof.

In some embodiments, R$^1$ of Formula (I) is phenyl. In other embodiments, R$^1$ of Formula (I) is selected from the group consisting of:

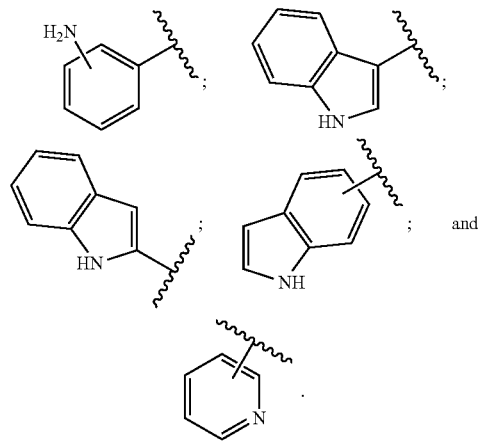

In some embodiments, R$^1$ is phenyl; n=2, saturated; R$^2$ is H and R$^3$ is alkyl, for example:

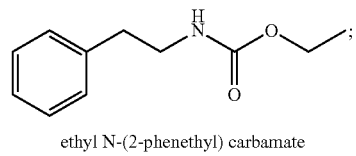

ethyl N-(2-phenethyl) carbamate or an agriculturally acceptable salt thereof.

In some embodiments, the compound is a compound of Formula (I)(a):

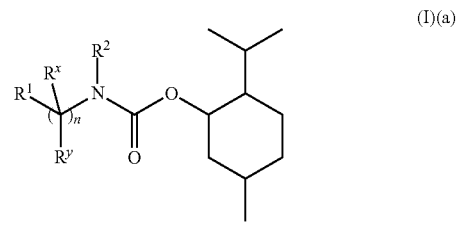

wherein:
R$^1$ is an aryl, an amine-substituted aryl, or a heteroaryl having at least one nitrogen atom;
n=0 to 10, saturated or unsaturated;
each occurrence of R$^x$ and R$^y$ is present or absent (depending upon chain saturation), and is each independently H or alkyl; and
R$^2$ is selected from the group consisting of: H, alkyl, alkenyl and alkynyl, or an agriculturally acceptable salt thereof.

In some embodiments, R$^1$ of Formula (I)(a) is phenyl. In other embodiments, R$^1$ of Formula (I)(a) is selected from the group consisting of:

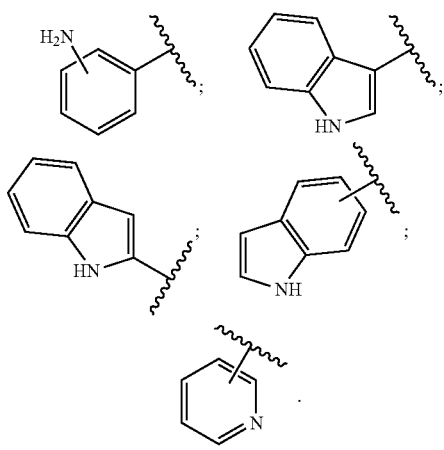

In some embodiments, the compound is a compound of Formula (I)(a)(i):

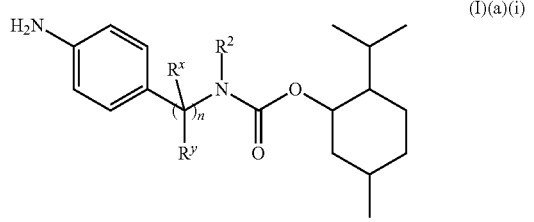

wherein:

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or an agriculturally acceptable salt thereof.

In some embodiments, the compound is a compound of Formula (I)(a)(ii):

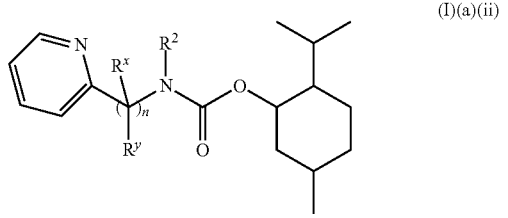

wherein:

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or an agriculturally acceptable salt thereof.

In some embodiments, the compound is a compound of Formula (I)(a)(iii):

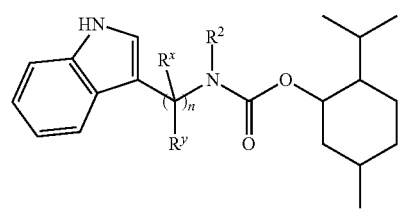

wherein:

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or an agriculturally acceptable salt thereof.

In some embodiments, the compound is a compound of Formula (I)(a)(iv):

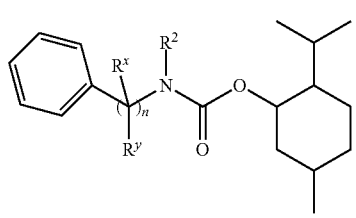

wherein:

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or an agriculturally acceptable salt thereof.

In some embodiments, the compound is selected from the group consisting of:

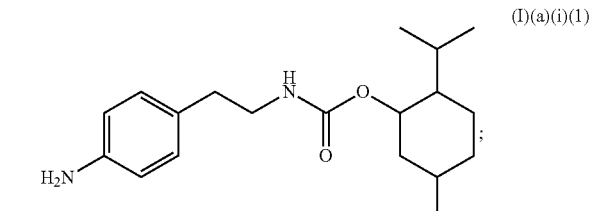

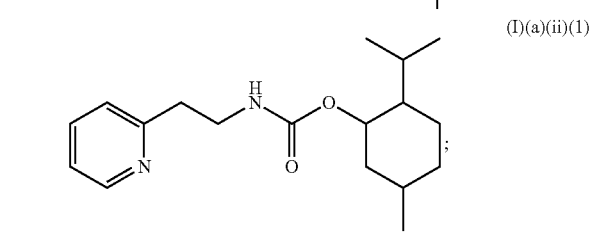

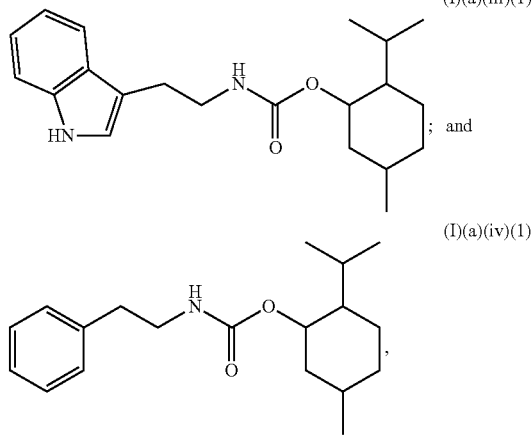

or an agriculturally acceptable salt thereof.

In some embodiments, the plant is a fruit or a vegetable crop plant.

In some embodiments, the plant is a citrus tree, and the compound is applied in an amount effective to treat or control a bacterial disease selected from the group consisting of canker, bacterial spot, Black Pit (fruit), Blast, citrus variegated chlorosis, and Citrus Huanglongbing. In some embodiments, the citrus tree is selected from the group consisting of orange, grapefruit, Mandarin, lemon, lime and Kumquat.

In some embodiments, the plant is a pome fruit, and the compound is applied in an amount effective to treat or control a bacterial disease selected from the group consisting of Fire Blight, Crown Gall, Blister spot and Hairy root. In some embodiments, the pome fruit is selected from the group consisting of apple, pear, quince, Asian pear, and loquats.

In some embodiments, the plant is a Musa species such as a banana, and the compound is applied in an amount effective to treat or control *Ralstonia solanacearum*.

In some embodiments, the plant is a cole (Brassicaceae) such as cabbage or broccoli, and the compound is applied in an amount effective to treat or control black rot (*Xanthomonas campestris*).

In some embodiments, the plant is a winegrape, and the compound is applied in an amount effective to treat or control for Pierce's disease (*Xylella fastidosa*) or crown gall (*Agrobacterium vitas, A. tumefaciens*).

In some embodiments, the plant is a stone fruit or nut (e.g., peaches, nectarines, plums, almonds, walnuts), and the compound is applied in an amount effective to treat or control bacterial spot and/or blight caused by *Xanthomonas arboricola*; blight caused by *Pseudomonas syringae*); crown gall caused by *Agrobacterium tumefaciens*; phony peach and plum; or almond leaf scorch caused by *Xylella fastidosa*.

In some embodiments, the plant is a landscape and/or shade tree (e.g., oak, maple, birch, etc.) for bacterial leaf scorch disease (e.g., cause by *Xylella fastidosa*).

In some embodiments, the plant is a potato, and the compound is applied in an amount effective to treat or control soft rot or black leg (*Erwinia*, Pectobacterium).

In some embodiments, the plant is a pepper plant, and the compound is applied in an amount effective to treat or control a bacterial disease selected from the group consisting of Bacterial Spot, Bacterial wilt, Bacterial canker, and Syringae seedling blight and leaf spot.

In some embodiments, the plant is a tomato plant, and the compound is applied in an amount effective to treat or control a bacterial disease selected from the group consisting of: bacterial canker, bacterial speck, bacterial spot, bacterial stem rot and fruit rot, Bacterial wilt, Pith necrosis, and Syringae leaf spot.

In some embodiments, the plant is a soybean plant, and the compound is applied in an amount effective to treat or control a bacterial disease selected from the group consisting of Bacterial blight, Bacterial pustules, Bacterial wilt, Bacterial crinkle leaf, Bacterial tan spot, and Wildfire.

In some embodiments, the plant is corn, and the compound is applied in an amount effective to treat or control a bacterial disease selected from the group consisting of: Bacterial leaf blight, stalk rot, bacterial stripe, chocolate spot, holcus spot all causes by *Pseudomonas* species, Bacterial leaf spot caused by *Xanthomomas* species, Bacterial stalk rot, top rot and Stewart's disease caused by *Erwinia* species, seed rot-seedling blight caused by *Bacillus* species, Purple leaf sheath caused by Hemiparasitic bacteria, Corn stunt caused by *Spriroplasma kunkelii*, Goss's bacterial wilt and blight caused by *Clivibacter michiganensis*.

In some embodiments, the plant is cotton, and the compound is applied in an amount effective to treat or control a bacterial disease selected from the group consisting of Bacterial blight caused by *Xanthomonas* species, and Crown gall caused by *Agrobacterium* species and Lint degradation caused by *Erwinia* species.

In some embodiments, the plant is wheat, and the compound is applied in an amount effective to treat or control a bacterial disease selected from the group consisting of Bacterial leaf blight, bacterial sheath rot and Basal glume rot caused by *Pseudomonas* species, Bacterial mosaic and Spike blight caused by *Clavibacter* species, Black chaff caused by *Xanthomonas* species, and Pink seed caused by *Erwinia* (Pantoea) species.

In some embodiments, the plant is rice, and the compound is applied in an amount effective to treat or control a bacterial disease selected from the group consisting of bacterial blight and leaf streak caused by *Xanthomonas* species, Foot rot caused by *Erwinia* species, Grain rot caused by *Burkholderia* species, and Sheath brown rot caused by *Pseudomonas* species.

In some embodiments, the plant is pineapple, and the compound is applied in an amount effective to treat or control a bacterial disease selected from the group consisting of bacterial heart rot, fruit collapse, bacterial fruitlet brown rot, marbled fruit, pink fruit and soft rot caused by *Erwinia* species, and Acetic souring caused by Acetic acid bacteria.

In some embodiments, the plant is turfgrass, and the compound is applied in an amount effective to treat or control a bacterial disease (e.g., bacterial wilt caused by *Poe annua*).

In some embodiments, the plant is an ornamental species (plants grown for decorative purposes, e.g., flowers, shrubs, broad-leafed trees and evergreens, such as conifers), and the compound is applied in an amount effective to treat or control a bacterial disease selected from the group consisting of: Bacterial leaf spots, blights, and Bacterial soft rot.

In some embodiments, the microbial biofilm formation or microbial infection is caused by a fungus. In some embodiments, the compound is applied to the plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice.

In some embodiments, the plant is citrus, and the compound is applied in an amount effective to treat or control a fungal disease selected from the group consisting of: *Alternaria* brown spot caused by *Alternaria alternaria*, Brown rot caused by *Phytophtora citricola*, Greasy spot and Greasy spot rind blotch caused by *Mycosphaerella citri*, Melanose caused by *Diaporthe citri*, *Phytophthora* foot rot, gummosis and root rot caused by *Phytophthora citrophthora*, *Phytophthora palmivora*, *Phytophthora syringae* and other *Phytophthora* spp, Post bloom fruit drop caused by *Colletotrichum acutatum*, and Scab caused by *Elsinoe fawcettii*.

In some embodiments, the plant is pome fruit, and the compound is applied in an amount effective to treat or control a fungal disease selected from the group consisting of: Apple scab caused by *Venturia inaequalis*, Bitter rot caused by *Colletotrichum gloeosporioides*, Diplodia canker caused by *Diplodia mutila*, *Phytophthora* crown, collar, root and fruit rot caused by *Phytophthora* spp., Powdery mildew caused by Podosphaera leucotricha, Pacific Coast pear rust, Cedar apple rust, Quince rust caused by *Gymnosporangium* spp., and Flyspeck caused by *Schizothyrium pomi*.

In some embodiments, the plant is peppers, and the compound is applied in an amount effective to treat or control a fungal disease selected from the group consisting of: Anthracnose caused by *Colletotrichum* spp., Damping-off and root rot caused by *Rhizoctonia solani*, *Phytophthora* spp., *Fusarium* spp., and *Pythium* spp., *Phytophthora* blight caused by *Phytophthora capsici*, and *Verticillium* wilt caused by *Verticillium albo-atrium*.

In some embodiments, the plant is tomato, and the compound is applied in an amount effective to treat or control a fungal disease selected from the group consisting of: *Alternaria* stem canker caused by *Alternaria alternaria*, Anthracnose caused by *Colletotrichum* spp., *Fusarium* crown, root rot and wilt caused by *Fusarium oxysporum*, Gray mold caused by *Botrytis cinerea*, Late blight caused by *phytophthora infestans*, *Pythium* damping-off and fruit rot caused by *Pythium* spp., *Rhizoctonia* damping-off and fruit rot caused by *Rhizoctonia solani*, *Septoria* leaf spot caused by *Septoria lycopersici*, *Verticillium* wilt caused by *Verticillium albo-atrum*, and White mold caused by *Sclerotinia sclerotiorum*.

In some embodiments, the plant is soybean, and the compound is applied in an amount effective to treat or control a fungal disease selected from the group consisting of: *Phytophthora* root and stem rot caused by *Phytophthora sojae*, *Pythium* root rot, damping-off and seed decay caused by *Pythium* spp., Brown stem rot caused by *Phialophora gregata*, *Rhizoctonia* root and stem rot caused by *Rhizoctonia solani*, Stem canker, pod and stem blight caused by *Diaporthe phaseolorum*, *Phomopsis* seed decay caused by *Phomopsis longicolla*, Charcoal rot caused by *Macrophomina phaseolina*, *Sclerotinia* stem rot caused by *Sclerotinia sclerotiorum*, Sudden death syndrome caused by *Fusarium solani*, and Soybean Rust caused by *Phakopsora pachyrhizi*.

In some embodiments, the plant is grape, and the compound is applied in an amount effective to treat or control a fungal disease selected from the group consisting of: *Alternaria* rot caused by *Alternaria alternaria*, Angular leaf spot caused by *Mycosphaerella angulata*, *Botrytis* bunch rot and blight caused by *Botrytis cinerea*, *Diplodia* cane dieback and bunch rot caused by *Diplodia natalensis*, Downy mildew caused by *Plasmopara viticola*, *Phytophthora* crown and root rot caused by *Phytophthora* spp., Powdery mildew caused by *Uncinula necator*, Ripe rot caused by *Glomerella cingulata*, *Septoria* leaf spot caused by *Septoria ampelopsidis*, and *Verticillium* wilt caused by *Verticillium dahliae*.

In some embodiments, the plant is potato, and the compound is applied in an amount effective to treat or control a fungal disease selected from the group consisting of: Brown spot, Black pit and Early blight caused by *Alternaria* spp., *Fusarium* dry rot and wilt caused by *Fusarium* spp., Gangrene caused by *Phoma* spp., Late blight and Pink rot caused by *Phytophthora* spp., *Rhizoctonia* canker and black scurf caused by *Rhizoctonia solani*, *Rosellinia* black rot caused by *Rosellinia* spp., *Septoria* leaf spot caused by *Septoria lycopersici*, Stem rot caused by *Sclerotium rolfsii*, *Verticillium* wilt caused by *Verticillium albo-atrum*, and White mold caused by *Sclerotinia sclerotiorum*.

In some embodiments, the plant is pineapple, and the compound is applied in an amount effective to treat or control a fungal disease selected from the group consisting of: Anthracnose caused by *Colletotrichum ananas*, Butt rot and White leaf spot caused by *Chalara paradoxa*, Leaf spot caused by *Curvularia eragrostidis*, *Phytophthora* heart rot caused by *Phytophthora cinnamomi* and *Phytophthora parasitica*, Root rot and Seedling blight caused by *Pythium* spp., and Leaking brown ring caused by *Tofflieadis dimenationa*.

In some embodiments, the plant is cotton, and the compound is applied in an amount effective to treat or control a fungal disease selected from the group consisting of: Anthracnose caused by *Glomerella gossypii*, Boll rot caused by *Colletotrichum gossypii*, *Fusarium* spp., *Phytophthora* spp., or *Rhizoctonia solani*, *Fusarium* wilt caused by *Fusarium oxysporum*, Leaf spot caused by *Alternaria* spp., *Cercospora gossypina*, *Rhizoctonia solani*, and *Stemphylium solani*, Lint contamination caused by *Aspergillus flavus*, Powdery mildew caused by *Leveillula taurica*, Cotton rust caused by *Puccinia schedonnardii*, Southwestern cotton rust caused by *Puccinia cacabata*, Tropical cotton rust caused by *Phakopsora gossypii*, Southern blight caused by *Sclerotium rolfsii*, Seedling disease complex caused by *Colletotrichum gossypii*, *Fusarium* spp., *Pythium* spp., *Rhizoctonia solani*, or *Thielaviopsis basicola*, Stem canker caused by *Phoma exigua*, and *Verticillium* wilt caused by *Verticillium dahliae*.

In some embodiments, the plant is corn, and the compound is applied in an amount effective to treat or control a fungal disease selected from the group consisting of: Anthracnose caused by *Colletotrichum graminicola*, *Aspergillus* ear and kernel rot caused by *Aspergillus flavus*, Banded leaf, sheath spot, root rot and stalk rot caused by *Rhizoctonia solani*, Brown spot, Black spot and Stalk rot caused by *Physoderma maydis*, *Curvularia* leaf spot caused by *Curvularia clavata*, *Diplodia* ear rot, stalk rot, seed rot and seedling blight caused by *Diplodia* spp., Downey mildews caused by *Sclerophthora* spp. or *Peronosclerospora* spp., Ear rots caused by *Alternaria alternaria*, Ergot caused by *Claviceps gigantea*, *Fusarium* ear, stalk, kernel, root, seed rot, seedling blight caused by *Fusarium* spp., *Cercospora* leaf spot caused by *Cercospora zeae-maydis*, *Helminthosporium* ear rot caused by *Helminthosporium carbonum*, *Pythium* root rot and stalk rot caused by *Pythium* spp., *Rhizoctonia* ear rot caused by *Rhizoctonia zeae*, Common corn rust and Southern corn rust caused by *Puccinia* spp., Southern blight caused by *Athelia rolfsii*, Common smut caused by *Ustilago zeae*, Southern corn leaf blight and stalk rot caused by *Cochliobolus heterostrophus*, and storage rots caused by *Aspergillus* spp. and *Penicillium* spp.

In some embodiments, the plant is rice, and the compound is applied in an amount effective to treat or control a fungal disease selected from the group consisting of: Black kernel caused by *Curvularia lunata*, Blast caused by *Pyricularia oryzae*, Brown spot caused by *Cochliobolus miyabeanus*, Downy mildew caused by *Sclerophthora macrospora*, False smut caused by *Ustilaginoidea vixens*, Narrow brown leaf spot caused by *Cercospora janseana*, Pecky rice caused by *Fusarium* spp., *Microdochium oryzae*, or *Sarocladium oryzae*, Root rot caused by *Fusarium* spp, or *Pythium* spp., Seedling blight caused by fungi (e.g., *Cochliobolus miyabeanus, Curvularia* spp., *Fusarium* spp., *Rhizoctonia solani, Sclerotium rolfsii* and *Athelia rolfsii*), Stackburn caused by *Alternaria padwickii*, Stem rot caused by *Magnaporthe salvinii*, Water-mold (seed-rot and seedling disease) caused by *Achlya* spp., *Fusarium* spp., or *Pythium* spp.

In some embodiments, the plant is wheat, and the compound is applied in an amount effective to treat or control a fungal disease selected from the group consisting of: *Alternaria* leaf blight caused *by Alternaria triticina*, Anthracnose caused by *Colletotrichum graminicola*, Black head molds caused by *Cladosporium* spp., *Epicoccum* spp., *Sporobolomyces* spp. or *Stemphylium* spp., Common bunt caused by *Tilletia* spp., Crown rot, seedling blight and dryland root rot caused by *Fusarium* spp. or *Gibberella* spp., Downey mildew caused by *Sclerophthora macrospora*, Dwarf bunt caused by *Tilletia controversa*, Ergot caused by *Claviceps purpurea*, Eyespot caused by *Tapesia yallundae*, Leaf rust caused by *Puccinia triticina*, Loose smut caused by *Ustilago tritici*, Microscopia leaf spot caused by *Phaeosphaeria microscopia*, Phoma spot caused by *Phoma* spp., Powdery mildew caused by *Erysiphe graminis, Pythium* root rot, Snow rot caused by *Pythium* spp., *Rhizoctonia* root rot caused by *Rhizoctonia solani*, Scab (head blight) caused by *Fusarium* spp. or *Gibberella* spp., Southern blight caused by *Sclerotium rolfsii*, Speckled snow mold caused by *Typhula* spp., Stem rust caused by *Puccinia graminis*, storage molds caused by *Aspergillus* spp. or *Penicillium* spp., Take-all caused by *Gaeumannomyces graminis*, and Zoosporic root rot caused by *Lagena radicola*.

In some embodiments, the plant is turfgrass (e.g., bahiagrass, bentgrass such as creeping bentgrass, bermudagrass, bluegrass such as Kentucky bluegrass or rough bluegrass, buffalograss, carpetgrass, centipedegrass, fescue such as fine fescue or tall fescue, ryegrass such as annual ryegrass or perennial ryegrass, St. Augustinegrass, zoysiagrass, etc.), and the compound is applied in an amount effective to treat or control a fungal disease selected from the group consisting of: Anthracnose caused by *Colletotrichum cereale*, Brown blight caused by *Drechslera siccans*, Brown patch caused by *Rhizoctonia solani*, Copper spot caused by *Gloeocercospora sorghi*, Damping off caused by *Pythium* or *Rhizoctonia* spp., Dollar spot caused by *Sclerotinia homoeocarpa*, Fairy ring caused by *Basidiomycetes*, Gray leaf spot caused by *Pyricularia grisea*, Gray snow mold caused by *Typhula incarnata* or *Typhula ishikariensis*, Large patch caused by *Rhizoctonia solani*, Leaf spot/Melting out caused by *Drechslera poae* or *Bipolaris cynodontis, Microdochium* patch caused by *Microdochium nivale*, Net blotch caused by *Drechslera dictyoides*, Pink snow mold caused by *Microdochium nivale*, Powdery mildew caused by *Blurmeria graminis, Pythium* blight caused by *Pythium aphanidermatum, Pythium* root dysfunction caused by *Pythium volutum, Pythium* root rot caused by *Pythium* spp., Red leaf spot caused by *Drechslera erythrospila*, Red thread caused by *Laetisaria fuciformis*, Rust caused by *Puccinia* spp., Slime mold caused by *Myxomycetes* spp., Spring dead spot/Necrotic ring spot caused by *Ophiosphaerella korrae* or *Ophiospaerella herpotricha*, Summer patech caused by *Magnaporthe poae*, White patch/white blight caused by *Melanotus phillipsii*, Yellow patch caused by *Rhizoctonia cerealis*, and Yellow tuft/downy mildew caused by *Scleropthora macrospora*.

In some embodiments, the plant is an ornamental species (plants grown for decorative purposes, e.g., flowers, shrubs, broad-leafed trees and evergreens, such as conifers), and the compound is applied in an amount effective to treat or control a fungal disease selected from the group consisting of: Fungal foliar blights and leaf spots, Blight caused by *Phytophthora* spp., Downy mildew, Powdery mildew, Rusts, Root rot caused by *Cylindrocladium* spp., Rot and wilt caused by *Fusarium* spp., Rot caused by *Gliocladium* spp., Crown rot or root rot caused by *Myrothecium* spp., Rot caused by *Pythium* spp. or *Phytophthora* spp., Rot caused by *Rhozoctonia* spp., Blight or stem rot caused by *Sclerotinia* spp. or *Sclerotium* spp., Rot caused by *Stromatinia* spp., and Root rot caused by *Thielaviopsis* spp.

In some embodiments, the microbial biofilm formation or microbial infection is caused by a phototroph, and an active compound is applied in an amount effective to treat or control a phototroph selected from the group consisting of: *Anabaena* spp. (e.g., *Anabaena circinalis, Anabaena flosaquae*), *Aphanizomenon* spp. (e.g., *Aphanizomenon flosaquae*), *Aphanocapsa* spp., *Cylindrospermopsis* spp. (e.g., *Cylindrospermopsis raciborskii*), *Lyngbya* spp., *Merismopedia* spp., *Microcystis* spp. (e.g., *Microcystis aeruginosa, Microcystis viridis, Microcystis wesenbergii*), *Nodularia* spp. (e.g., *Nodularia harveyana, Nodularia spumigena*), *Nostoc* spp., *Oscillatoria* spp., *Planktothrix* spp., *Phormidium* spp. (e.g., *Phormidium tenue*), *Pseudanabaena* spp., *Raphidiopsis* spp., *Synechosystis* spp., and *Synechococcus* spp.

A further aspect of the present disclosure is an agricultural composition comprising: (a) an agriculturally acceptable carrier (e.g., an aqueous carrier or a solid particulate carrier); and (b) an antimicrobial or biofilm preventing, removing or inhibiting compound described herein, or an agriculturally acceptable salt thereof. In some embodiments, the composition further includes a microbicide (e.g., a bactericide, fungicide or algaecide). In some embodiments, the microbicide comprises copper (e.g., copper hydroxide). In some embodiments, the microbicide comprises an antibiotic or a bacteriophage. In some embodiments, the composition further includes a plant defense activator. In some embodiments, the composition further includes both a plant defense activator and a microbicide.

Further provided are methods of enhancing the effects of a microbicide comprising applying an active compound described herein, in combination with said microbicide (e.g., a bactericide, fungicide or algaecide). In some embodiments, the microbicide comprises copper (e.g., copper hydroxide). In some embodiments, the microbicide is an antibiotic or a bacteriophage. In some embodiments, the applying step is carried out by applying the active compound and the microbicide simultaneously. In some embodiments, the applying step is carried out by applying the active compound and the microbicide sequentially.

Also provided are methods of enhancing the effects of a plant defense activator comprising applying an active compound described herein, in combination with said plant defense activator. In some embodiments, the applying step is carried out by applying the active compound and the microbicide simultaneously. In some embodiments, the applying step is carried out by applying the active compound and the microbicide sequentially.

Still further provided are methods of controlling phototroph growth in an aquatic site, comprising applying to said site (e.g., adding to the water) a treatment effective amount of an active compound as described herein. Compositions comprising an active compound and another algaecide are also provided. Also provided are methods of reducing, inhibiting the formation, or inhibiting the growth of cyanobacteria or a cyanobacterial bloom. Methods of enhancing the effects of an algaecide are provided, comprising applying an active compound in combination with said algaecide (e.g., simultaneously or sequentially).

A further aspect of the present disclosure is an antimicrobial or biofilm preventing, removing or inhibiting compound as described herein, for use in treating or preventing a bacterial or fungal infection in a plant or plant part and/or phototroph infestation as described above and below.

DETAILED DESCRIPTION OF EMBODIMENTS

The present disclosure relates to compounds, compositions and methods useful for controlling or combating biofilms or microbial infection in a plant or plant part, or environment where plants may grow. All patent references referred to in this patent application are hereby incorporated by reference in their entirety as if set forth fully herein.

A. Definitions

"Active compound" as used herein refers to the various embodiments of compounds described in Section B (carbamates) set forth below.

"Plant" as used herein includes all members of the plant kingdom, including higher (or "vascular") plants and lower ("non-vascular") plants, and particularly including all plants in the divisions Filicinae, Gymnospermae (or "gymnosperm"), and Angiospermae (or "Angiosperm") Nonvascular plants of the present disclosure include, but are not limited to, bryophytes.

A plant of the present disclosure includes, but is not limited to, a crop plant, a turfgrass, an ornamental species, a species grown for timber or pulp, a species grown for biofuels or species grown for pharmaceuticals. Additionally, plants of the present disclosure include, but are not limited to, tobacco, tomato, potato, sugar beet, pea, carrot, cauliflower, broccoli, soybean, canola, sunflower, alfalfa, cotton, rapeseed, Arabidopsis, peach, pepper, apple, chili, peanut, orange, grape, coffee, cassava, spinach, lettuce, cucumber, wheat, maize, rye, rice, turfgrass, oat, barley, sorghum, millet, sugarcane, or banana.

"Angiosperm" as used herein includes, but is not limited to, plants of the sub-classes Monocotyledoneae (or monocots) and Dicotyledoneae (or dicots).

Monocotyledoneae (or monocots) as used herein includes but is not limited to Amaryllidaceae—the Amaryllis Family, Gramineae (Poaceae)—the Grass Family, Liliaceae—the Lily Family, Orchidaceae—the Orchid Family, Palmae (Aracaceae)—the Palm Family; and Lemnacea—the duckweed family.

Dicotyledoneae (or dicots) as used herein includes but is not limited to Cactacae—the Cactus Family, Compositae (Asteraceae)—the Sunflower Family, Cruciferae (Brassicaceae)—the Mustard Family, Cucurbitaceae—the Gourd Family, Ericaceae—the Heath Family, Euphorbiaceae—the Spurge Family, Lauraceae—the Laurel Family, Leguminosae (Fabaceae)—the Pea Family, Rosaceae—the Rose Family, Rutaceae—the Rue Family, Solanaceae—the Nightshade Family, and Umbelliferae (Apiaceae)—the Carrot family.

Gymnospermae (or "Gymnosperms") as used herein includes but is not limited to conifers.

"Conifer," as used herein, refers to a member of the order Coniferae in the sub-phylum Gymnospermae in the phylum Spermaphyta. Exemplary conifers which may be used in practicing the present disclosure are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*); and Western larch (*Laryx occidentalis*). See, e.g., U.S. Pat. No. 5,122,466 to Stomp et al.

"Duckweed" as used herein includes plants of the genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wolfiella* (*Wl. caudata, Wl. denticulata, Wl. gladiata, Wl. hyalina, Wl. lingulata, Wl. repunda, Wl. rotunda, and Wl. neotropica*). See, e.g., U.S. Pat. No. 7,161,064 to Stomp et al.

Particular examples of plants include but are not limited to all cereal and grain crops, herbs and spices, oil seed crops, sugarcane, vegetable crops, brassica vegetables, bulb vegetables, cucurbit vegetables and fruit, leafy vegetables, fruiting vegetables, legume vegetables, root and tuber vegetables, tree, vine and shrub crops, berry crops, citrus (e.g., orange, grapefruit, Mandarin (including Tangerine and Satsuma), lemon, lime, and kumquat), pome fruit (e.g., apple, pear, quince, Asian pear, loquat, etc.), stone fruit (e.g., peach, apricot, prune, plum, cherries, almond, etc.), miscellaneous tree food crops, non-food tree crops, tree nuts, tropical and subtropical trees and fruit, vine crops, pasture grasses, forage legumes, and rangeland, grass seed or sod production, pastures, cotton, corn, soybeans, rice, wheat, greenhouse/shadehouse grown plants, ornamental, plant nurseries, Christmas trees, golf courses and other commercial or residential turf areas such as athletic fields, lawns, municipal areas and cemeteries, or other ornamental turf areas, forestry, tobacco, orchids, flowers and roses, foliage crops, algae such as green algae, bryophytes (mosses, liverworts, hornworts, etc. Note that "foliage crops" refers to the types of plants (ferns, etc.) that are typically used in home or commercial settings for decorative purposes; this alone constitutes a very large commercial industry.

"Plant part" as used herein refers to seeds, roots, leaves, shoots, fruits (e.g., apples, pineapples, citrus fruit, etc.), vegetables, tubers, flowers (e.g., cut flowers such as roses, as well as the reproductive parts of plants), petals, stem, trunk, etc., harvested or collected from a plant as described herein.

The plant part of a vascular plant may be a non-vascular part, such as a seed or meristem (growing tip of a shoot).

"Applying" as described herein can be carried out directly or indirectly by any suitable technique, including topically or systemically applying to the plant or plant part, applying to the media in which the plant or plant part is grown, stored, displayed or maintained (e.g., adding to water in which the stems of cut flowers are placed), etc. Note that the plant may be grown in any suitable media, including but not limited to soil, potting soil, soilless media such as sand, hydroponic media (including solution culture, medium culture, deep water culture, aeroponic culture), etc.

"Agricultural composition" as described herein may be in any suitable form, including but not limited to: wettable powders, dry flowables, soluble powders, water dispersibles, liquids, dusts, emulsifiable concentrates, flowables, fumigants, water dispersible granules, liquid concentrates, granules, water soluble packages, wettable powders in water soluble films, emulsions, etc.

"Carbamate" refers to the commonly known moiety:

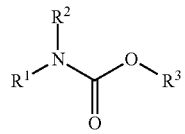

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent, for example, an acetyl group, a propionyl group, a butyroyl group, a benzoyl group, or an alkylbenzoyl group.

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

As used herein, the identification of a carbon number range, e.g., C1-C12 alkyl, is intended to include each of the component carbon number moieties within such range, so that each intervening carbon number and any other stated or intervening carbon number value in that stated range is encompassed, such that sub-ranges of carbon number within specified carbon number ranges may independently be specified. For example, C1-C12 alkyl is intended to include methyl, ethyl, propyl, butyl, pentyl, hexyl, heptyl, octyl, nonyl, decyl, undecyl and dodecyl, including straight chain as well as branched groups, as noted above, and the carbon number range C1-C12 alkyl may also be more restrictively specified as sub-ranges such as C1-C4 alkyl, C2-C8 alkyl, C2-C4 alkyl, C3-C5 alkyl, or any other sub-range within the broader carbon number range. In addition, ranges of carbon numbers specifically excluding a carbon number or numbers are contemplated, as are sub-ranges excluding either or both of carbon number limits of specified ranges.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

As understood in the art, the term "optionally substituted" indicates that the specified group is either unsubstituted, or substituted by one or more suitable substituents. A "substituent" that is "substituted" is an atom or group which takes the place of a hydrogen atom on the parent chain or cycle of an organic molecule.

"Heterocyclo," as used herein, refers to a monocyclic, bicyclic or tricyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this disclosure can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms (e.g., N, O or S). If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

An "amine" or "amino" is intended to mean the group —NH$_2$.

An "amide" as used herein refers to a functional group having a carbonyl group (C=O) linked to a nitrogen atom (N), or an organic compound that contains this group, generally depicted as:

wherein, R and R' can independently be any covalently-linked atom or atoms.

A "thiol" or "mercapto" refers to an —SH group or to its tautomer =S.

A "sulfone" as used herein refers to a sulfonyl functional group, generally depicted as:

wherein, R can be any covalently-linked atom or atoms.

A "sulfoxide" as used herein refers to a sulfinyl functional group, generally depicted as:

wherein, R can be any covalently-linked atom or atoms.

The term "oxo," as used herein, refers to a =O moiety.
The term "oxy," as used herein, refers to a —O— moiety.
"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —CO$_2$H or —(C=O)—OH.

It will be understood that the compounds, compositions and methods provided herein may be further specified in some embodiments by provisos or limitations excluding specific substituents, groups, moieties, structures, ingredients, steps, or conditions, as applicable, in relation to various broader specifications and exemplifications set forth herein. Accordingly, the disclosure contemplates restrictively defined compounds, for example, having a proviso such as a compound wherein $R^i$ is C1-C12 alkyl, with the proviso that $R^i \neq$ C4 alkyl when $R^j$ is alkenyl.

"Agriculturally acceptable salt" is intended to mean a salt that retains the biological effectiveness of the free acids and bases of a specified compound and that is not biologically or otherwise undesirable. Examples of agriculturally acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

B. Active Compounds

Active compounds are provided below. In some of the embodiments provided in the present disclosure, active compounds are carbamates. Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g., asymmetric carbon atoms. Thus, the present disclosure is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present disclosure unless otherwise specified. Also included in active compounds of the disclosure are tautomers (e.g., tautomers of triazole and/or imidazole) and rotamers. All chains defined by the formulas herein which include three or more carbons may be saturated or unsaturated unless otherwise indicated.

Provided herein are active compounds of Formula (I):

(I)

wherein:

$R^1$ is an aryl, an amine-substituted aryl, or $R^1$ is a heteroaryl having at least one nitrogen atom;

n=0 to 10, saturated or unsaturated;

each occurrence of $R^x$ and $R^y$ is present or absent (depending upon chain saturation), and is each independently H or alkyl;

$R^2$ is selected from the group consisting of: H, alkyl, alkenyl and alkynyl; and $R^3$ is alkyl, substituted or unsubstituted cycloalkyl, or an agriculturally acceptable salt thereof.

In some embodiments, $R^1$ is phenyl; n=2, saturated; $R^2$ is H and $R^3$ is alkyl, for example:

ethyl N-(2-phenethyl) carbamate or an agriculturally acceptable salt thereof.

In some embodiments of Formula (I), $R^3$ is a substituted cycloalkyl represented by Formula (I)(a):

(I)(a)

wherein:

$R^1$ is an aryl, an amine-substituted aryl, or a heteroaryl having at least one nitrogen atom;

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or an agriculturally acceptable salt thereof.

In some embodiments of Formula (I) and Formula (I)(a), $R^1$ is phenyl.

In some embodiments of Formula (I) and Formula (I)(a), $R^1$ is a group:

In some embodiments of Formula (I) and Formula (I)(a), $R^1$ is a heteroaryl having at least one nitrogen atom. Examples include, but are not limited to:

In some embodiments of Formula (I)(a), $R^1$ is an amine-substituted aryl represented by Formula (I)(a)(i):

(I)(a)(i)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or an agriculturally acceptable salt thereof.

In some embodiments of Formula (I)(a), $R^1$ is heteroaryl having at least one nitrogen represented by Formula (I)(a)(ii):

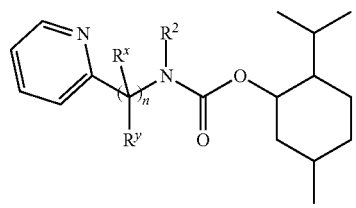

wherein:
n=0 to 10, saturated or, unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or an agriculturally acceptable salt thereof.

In some embodiments of Formula (I)(a), $R^1$ is heteroaryl having at least one nitrogen represented by Formula (I)(a)(iii):

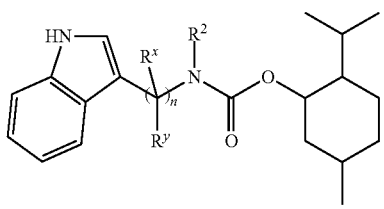

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or an agriculturally acceptable salt thereof.

In some embodiments of Formula (I)(a), $R^1$ is phenyl, which is represented Formula (I)(a)(iv):

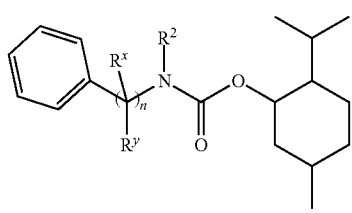

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or an agriculturally acceptable salt thereof.

Exemplary compounds of Formula (I)(a) are given below, in which $R^1$ is heteroaryl, or aryl substituted with amino; n=2, saturated, $R^x$ and $R^y$ are each H, $R^2$ is H, and $R^3$ is substituted cycloalkyl.

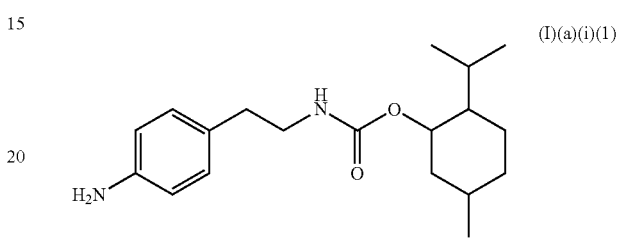

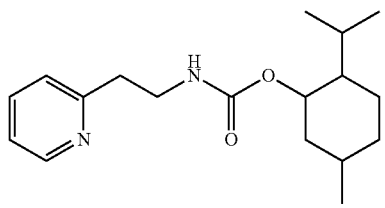

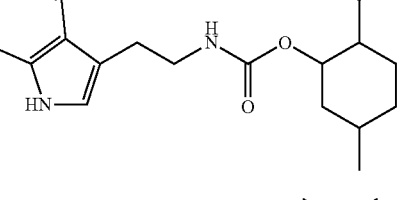

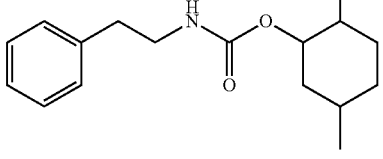

Also provided is an agriculturally acceptable salt thereof of each of the compounds represented by the Formulas described above. Each of the Formulas provided herein may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc., as desired.

C. Microbicides and Plant Defense Activators

In some embodiments, an active compound described herein is applied in combination with a microbicide. "Microbicide" as used herein refers to a substance with the ability to kill or to inhibit the growth of microorganisms (e.g., bacteria (including cyanobacteria), fungal cells, protozoa, algae, etc.), which microbicide is not an active compound in the group herein disclosed of triazole derivatives. Common microbicides used for microbial control in plants include copper compounds. Examples of copper compounds include, but are not limited to, Bordeaux mixture, copper hydroxide, copper oxychloride, copper sulfate, cuprous oxide, mancopper or oxine-copper. However, microorganisms (e.g., bacteria such as *Xanthomonas* and *Pseudomonas*) may become resistant to treatment with copper.

In some embodiments, resistant microorganisms (e.g., copper-resistant bacteria) are rendered more susceptible to a microbicides and/or the effectiveness of treatment with a microbicides is enhanced upon application in combination with an active compound described herein (e.g., fruit or vegetable yield is increased as compared to diseased plant producing the fruit or vegetable that is untreated or treated only with the microbicide).

Other microbicides include, but are not limited to, azoles such as azaconazole, bitertanol, bixafen, carpropamid, propiconazole, difenoconazole, diniconazole, cyproconazole, epoxiconazole, fluquinconazole, flusilazole, flutriafol, hexaconazole, imazalil, imibenconazole, ipconazole, iprodione, tebuconazole, tetraconazole, fenbuconazole, metconazole, myclobutanil, perfurazoate, penconazole, paclobutrazol, prothioconazole, pyrimenthanil, bromuconazole, pyrifenox, prochloraz, spiroxamine, triadimefon, triadimenol, triflumizole or triticonazole; pyrimidinyl carbinoles such as ancymidol, fenarimol, fluopicolide, flurprimidol, or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl (mefanoxam), ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, boscalid, fenfuram, flutolanil, mepronil, oxycarboxin or thifluzamide; guanidines such as guazatine, dodine or iminoctadine; strobilurines such as azoxystrobin, fluoxastrobin, pyraclostrobin, picoxystrobin, oryzastrobin, dimoxystrobin, kresoximmethyl, metominostrobin, SSF-129, methyl 2[(2-trifluoromethyl)-pyrid-6-yloxymethyl]-3-methoxy-acrylate or 2-[{α[(α-methyl-3-trifluoromethyl-benzyl)imino]-oxyl}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, harpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, thiophanate-methyl, triazoxide, tricyclazole, triforine, validamycin, (S)-5-methyl-2-methylthio-5-phenyl-3-phenylamino-3,5-dihydroimidazol-4-o-ne (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

An "antibiotic" as used herein is a type of "microbicide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

Other microbicides that may be used in combination with the active compounds of the present disclosure include bacteriophages (bacterial viruses) such as *Bacillus*. Examples of bacteriophage microbicides include, but are not limited to, AgriPhage™ (OmniLytics, Inc., Salt Lake City, Utah) and Serenade® (AgraQuest, Davis, Calif.). See, e.g., U.S. Pat. Nos. 5,919,447 and 6,077,506 to Marrone et al.; U.S. Pat. No. 6,103,228 to Heins et al.; and U.S. Patent Application Publication 20080152684.

In some embodiments, an active compound described herein is applied in combination with a plant defense activator. A "plant defense activator" as used herein is a compound that improves disease resistance by activating a plant's natural defense mechanisms, e.g., induces the plant to produce disease-fighting compounds. Examples of plant defense activators include, but are not limited to, prohexadione-calcium (Apogee), Cropset (plant booster element complex), probenazole, potassium phosphate (e.g., ProPhyt®, Helena Chemical Company), harpin protein (e.g., Messenger®, Eden Biosciences Ltd, Bothell, Wash.), acibenzolar or acibenzolar-S-methyl (e.g., Actigard™, Syngenta Crop Production, Inc, Greensboro, N.C.), streptomycin sulfate, reynoutria sachalinensis extract (reysa), etc.

D. Agrochemical Compositions

Active compounds of the present disclosure can be used to prepare agrochemical compositions in like manner as other antimicrobial compounds. See, e.g., U.S. Pat. Application 2006/0094739; see also U.S. Pat. Nos. 6,617,330; 6,616,952; 6,569,875; 6,541,500, and 6,506,794.

Active compounds described herein can be used for protecting plants against diseases that are caused by microorganisms, including biofilm-forming microorganisms. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic microorganisms.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds can be used in the form of compositions and can be applied to the crop area or plant to be treated, simultaneously or in succession with further compounds and/or compositions. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Suitable carriers and adjuvants can be solid or liquid and are substances useful in formulation technology, e.g. natural or regenerated mineral substances, solvents, dispersants, wetting agents, tackifiers, thickeners, binders or fertilizers.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

The formulation, i.e. the compositions containing the active compound and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of a compound described herein, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

E. Methods of Use

Target crops or plants to be treated with active compounds and compositions of the disclosure typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, pineapple, turf (including grass species grown and maintained as turfgrass) and natural rubber plants, as well as ornamentals (flowers, shrubs, broad-leafed trees and evergreens, such as conifers). This list does not represent any limitation.

1. Bacterial infections. The methods, active compounds and compositions can be used to treat bacterial infections in a variety of plants, with specific examples including but not limited to those set forth below.

Citrus. In citrus trees (including orange, lemon, lime, and grapefruit) active compounds and compositions as described herein can be used to treat or control a variety of microbial diseases, including but not limited to canker (caused by *Xanthomonas campestris* or *Xanthomonas axonopodis* infection), bacterial spot (caused by *Xanthomonas campestris* pv. *Citrumelo* infection); Black Pit(fruit) (caused by *Pseudomonas syringae* infection); Blast (caused by *Pseudomonas syringae* infection) citrus variegated chlorosis (caused by *Xylella fastidiosa* infection), and Citrus Huanglongbing (HLB) caused by *Candidatus* Liberibacter asiaticus.

Pome Fruit. In pome fruits (including apple, pear, quince, Asian pear, and loquat), active compounds and compositions as described herein can be used to treat or control a variety of microbial infections, including but not limited to Fire Blight (caused by *Erwinia amylovora* infection), Crown Gall (caused by *Agrobacterium tumefaciens* infection); Blister spot (caused by *Pseudomonas syringae* infection) and Hairy root (caused by *Agrobacterium rhizogenes* infection).

Peppers. In pepper plants, active compounds and compositions as described herein can be used to treat or control a variety of microbial infections, including but not limited to:

Bacterial Spot (caused by *Xanthomonas campestris* pv. *vesicatoria* infection); Bacterial wilt (caused by *Ralstonia solanacearum* infection), and Syringae seedling blight and leaf spot (caused by *Pseudomonas sryingae* infection).

Tomatoes. In tomato plants, active compounds and compositions as described herein can be used to treat or control a variety of microbial infections, including but not limited to: Bacterial canker (caused by *Clavibacter michiganesis*), Bacterial speck (caused by *Pseudomonas syringae*), Bacterial spot (caused by *Xanthomonas campestris vesicatoria*), Bacterial stem rot and fruit rot (caused by *Erwinia carotovora*), Bacterial wilt (caused by *Ralstonia solanacearum*), Pith necrosis (caused by *Pseudomonas corrugate*), and Syringae leaf spot (caused by *Pseudomonas syringae*).

Soybeans. In soybeans, active compounds and compositions as described herein can be used to treat or control a variety of microbial infections, including but not limited to: Bacterial blight (caused by *Pseudomonas amygdale*), Bacterial pustules (caused by *Xanthomonas axonopodis* pv. *Glycines*), and Bacterial wilt (caused by *Ralstonia solanacearum* or *Curtobacterium flaccumfaciens*).

Corn, Cotton, Wheat and Rice. In corn, cotton, wheat and rice, active compounds and compositions as described herein can be used to treat or control a variety of microbial infections, including but not limited to: bacterial blights, leaf spots and leaf streak caused by *Xanthomonas* species; bacterial sheath rot, stripe and spot caused by *Pseudomonas* species; and to bacterial stalk and top rot, wilt, foot rot, pink seed and lint degradation caused by *Erwinia* species.

Pineapple. In pineapple, active compounds and compositions as described herein can be used to treat or control a variety of microbial infections, including but not limited to: Bacterial heart rot and Fruit collapse (caused by *Erwinia chrysanthemi*), Bacterial fruitlet brown rot (caused by *Erwinia ananas*), Marbled fruit and Pink fruit (caused by *Erwinia herbicola*), Soft rot (caused by *Erwinia carotovora*), and Acetic souring (caused by Acetic acid bacteria).

The above listing is but a sampling, and active compounds and compositions as described herein may also be used to treat or control bacteria (some of which are named above) in a variety of plants. For example, the bacteria *Xylella fastidiosa* infects citrus trees as noted above (citrus variegated chlorosis), and also infects grapevines (Pierce's disease). Other plant hosts of *Xylella fastidiosa* include, but are not limited to, ornamentals (bacterial leaf spot, fire blight, bacterial leaf scorch, etc.), oleander (leaf scorch), almond, coffee, maple, mulberry, elm, sycamore, alfalfa, etc. Similarly, *Ralstonia solanacearum* infects soybeans (bacterial wilt) as well as banana (Moko disease), tobacco (Granville wilt), geranium (southern bacterial wilt), potato (brown rot) and a wide variety of other plants, including ginger and mulberry and turfgrass (bacterial wilt).

2. Fungal infections. In addition to treating or controlling bacterial infections, active compounds and compositions as described herein can be used to treat or control fungal infections such as rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice. Genera of plant-pathogenic fungi that can be treated or controlled by the active compounds, compositions, and methods described herein include but are not limited to: *Pythium* spp., *Fusarium* spp., *Rhizoctonia* spp., *Cercospora* spp., *Alternaria* spp., *Colletotrichum* spp., *Ustilago* spp., *Phoma* spp., *Gibberella* spp. *Penicillium* spp., *Glomerella* spp. *Diplodia* spp., *Curvularia* spp., *Sclerospora* spp., *Peronosclerospora* spp., *Puccinia* spp., *Aspergillus* spp., *Phomopsis* spp., *Diaporthe* spp., *Botrytis* spp., *Verticillium* spp., and *Phytophthors* spp. Fungal genera also include: *Sclerophthora* spp., *Erysipthe* spp., *Sclerotinia* spp., *Pyricularia* spp., *Typhula* spp., *Microdochium* spp., *Helminthosporium* spp., *Gaeumannomyces* spp., *Ophiospaerella* spp., *Magnaporthe* spp., and *Thielaviopsis* spp.

Particular fungal infections that can be treated or controlled by the methods, compounds and compositions described herein, in vegetables and greenhouse crops, include *Phytophthora* blight (caused by *Phytophthora capsici*) and *Pythium* damping-off (caused by *Pythium* spp).

Note that *Phytophthora* also has adverse effects on crops ranging from pineapples to cotton. It can kill woody citrus seedlings and young citrus trees (oranges, grapefruits, lemons, limes). In the greenhouse, germinating seed and seedlings are very susceptible to damping-off caused by *Phytophthora, Pythium, Sclerotina* and *Rhizoctonia* species. The cost to the grower to lose his crop to any of these fungi is substantial. The loss can happen at transplant time or when the crop is ready to be harvested.

The problems of fungi are not restricted to traditional crops but also extend to forestry products and have worldwide scope. *Phytophthora cinnamomi* is a soil-borne water mould that leads to a condition in plants called "root rot" or "dieback." *P. cinnamomi* causes root rot affecting woody ornamentals including azalea, dogwood, forsythia, Fraser fir, hemlock, Japanese holly, juniper, rhododendron, white pine, and American chestnut. *P. cinnamomi* is responsible for the destruction of the elegant American chestnut tree. In Australia, *P. cinnamomi* has spread through the forests of western Australia, and into coastal forests of Victoria, where entire plant ecosystems are being obliterated. Given that *P. cinnamomi* is a soil-borne water mould that infects the roots, almost the entire action takes place below ground. This problem highlights the importance of developing new compounds to counter fungal infections, even those that directly affect only the roots of the plant rather than the more visible effects on fruits or vegetables.

Active compounds can be applied to plants or plant loci in accordance with known techniques. The compound(s) can be tank mixed with other agricultural, turf, ornamental nursery, forestry and all other plant-labeled compatible pesticides. The compound(s) can be applied to seed. The compound(s) can be applied to edible and non-edible crops. The compound(s) can be applied to roots and all other parts of all plants. The compound(s) can be applied in greenhouses. The compound(s) can be applied and used in food-processing facilities. The compound(s) can be applied to plastic food bags and containers. The compound(s) can be applied as a solid, as its free base, or as a salt. The salts can include, but are not limited to, HI, HCl, HBr, $H_2SO_4$, acetic acid, and trifluoroacetic acid. The compound(s) can be applied as a solution from 0.0001% to 99.9%. The compound(s) can be applied as a solid or solution with copper-based cidal compounds. The compound(s) can be applied with specific additional active agents, including but not limited to bactericides, fungicides, pesticides, biological insecticides and microbial insecticides.

Application can be carried out with any suitable equipment or technique, such as: Aerial—Fixed wing and Helicopter; Ground Broadcast Spray—Boom or boomless system, pull-type sprayer, floaters, pick-up sprayers, spray coupes, speed sprayers, and other broadcast equipment, water wagons and water bags; Low pressure boom sprayers, High pressure sprayers; Air blast sprayers; Low volume air sprayers (mist blowers); Ultra-low volume sprayers (ULV);

Aerosol Generators (foggers); Dusters; Soil Injector; Hand-Held or High-Volume Spray Equipment—knapsack and backpack sprayers, pump-up pressure sprayers, hand guns, motorized spray equipment; Selective Equipment—Recirculating sprayers, shielded and hooded sprayers; Controlled droplet applicator (CDA) hand-held or boom-mounted applicators that produce a spray consisting of a narrow range of droplet size; Any and all greenhouse sprayers; Microsprinkler or drip irrigation systems; Chemigation.

One method of applying an active compound, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

Advantageous rates of application are normally from 5 g to 2, 3, 4, 5, 8 or 10 kg of active ingredient (a.i.) per hectare (ha). In some embodiments, rates of application are from 10 g to 1 kg a.i./ha, or from 20 g to 600 g a.i./ha. When used as seed drenching agent, convenient dosages are from 10 mg to 1 g of active substance per kg of seeds. In some embodiments, rates of application are from 0.1 kg/ha to 10 kg/ha, or from 0.5 kg/ha to 5 kg/ha, or from 1 kg/ha to 3 kg/ha.

F. Combination Treatments

In some embodiments, methods of enhancing the effects of a microbicide (such as a microbicide comprising copper, e.g., Kocide® 2000 or Kocide® 3000 (DuPont™, with active ingredient copper hydroxide) are disclosed, comprising the step of applying an active compound in combination with a microbicide, the active compound being applied in an amount effective to enhance the effects of the microbicide.

In some embodiments, methods of enhancing the effects of a plant defense activator are disclosed, comprising the step of applying an active compound in combination with a plant defense activator, the active compound being applied in an amount effective to enhance the effects of the plant defense activator.

"Enhancing" the effects of a microbicide by applying an active compound in combination with the microbicide refers to increasing the effectiveness of the microbicide, such that the microorganism killing and/or growth inhibition is higher at a certain concentration of the microbicide applied in combination with the active compound than without. In some embodiments, a bacteria or other microorganism is "sensitized" to the effects of a microbicide, such that the bacteria or other microorganism that was resistant to the microbicide prior to applying the active compound (e.g., little to none, or less than 20, 10, 5 or 1% are killed upon application) is rendered vulnerable to that microbicide upon or after applying the active compound (e.g., greater than 20, 30, 40, 50, 60, 70, 80, 90, or 95% or more are killed).

Similarly, "enhancing" the effects of a plant defense activator by applying an active compound in combination with the plant defense activator refers to increasing the effectiveness of the plant defense activator, such that the microorganism killing and/or growth inhibition is higher at a certain concentration of the plant defense activator applied in combination with the active compound than without. In some embodiments, a bacteria or other microorganism is "sensitized" to the effects of a plant defense activator, such that the bacteria or other microorganism that was resistant to the effects of the plant defense activator prior to applying the active compound (e.g., little to none, or less than 20, 10, 5 or 1% are killed upon application) is rendered vulnerable to the effects of that plant defense activator upon or after applying the active compound (e.g., greater than 20, 30, 40, 50, 60, 70, 80, 90, or 95% or more are killed).

As used herein, the application of two or more compounds (inclusive of active compounds and microbicides) "in combination" means that the two compounds are applied closely enough in time that the application of or presence of one alters the biological effects of the other. The two compounds may be applied simultaneously (concurrently or contemporaneous) or sequentially. Applications according to some embodiments may be within a period of time that ranges from minutes (e.g., 1, 5, 10, 30, 60, or 90 minutes or more) to days (e.g., 1, 2, 5, 8 or 10 or more days), as appropriate for efficacious treatment.

Simultaneous, concurrent or contemporaneous application of the compounds may be carried out by mixing the compounds prior to application, or by applying the compounds at the same point in time but at different sites of the plant or using different types of applications, or applied at times sufficiently close that the results observed are indistinguishable from those achieved when the compounds are applied at the same point in time.

Sequential application of the compounds may be carried out by applying, e.g., an active compound, at some point in time prior to application of a microbicide, such that the prior application of active compound enhances the effects of the microbicide (e.g., percentage of microorganisms killed and/or slowing the growth of microorganisms). In some embodiments, an active compound is applied at some point in time prior to the initial application of a microbicide. Alternatively, the microbicide may be applied at some point in time prior to the application of an active compound, and optionally, applied again at some point in time after the application of an active compound.

The compounds, compositions and methods of the present disclosure may in particular implementations be constituted as comprising, consisting, or consisting essentially of, some or all of such features, aspects and embodiments, and various elements, ingredients, components, steps, and conditions may be further aggregated in whole or part to constitute various further implementations of the disclosure. For example, the compositions include those comprising, consisting of, or consisting essentially of (e.g., 50%, 60%, 70%, 80%, 90%, 95%, or 99% or more of the total weight or volume of the composition), a component such as an active compound and/or a biocide as provided herein.

G. Aquatics

In some embodiments, the microbial biofilm formation is caused by a phototroph (such as cyanobacteria or green algae), which may be present in a body of water (e.g., a pond (including a retention pond, detention pond, etc.), lake, pool, cooling tower, aquarium, etc.) or aquatic system (system through which water, or other fluid in which algae may grow, is stored and/or transported). The water or aquatic system may or may not also contain living plants. In some embodiments, a compound is applied to the water or other fluid in an amount effective to treat or control a cyanobacteria or other phototroph. For example, a compound may be applied to the water or other fluid in amount effective to reduce, inhibit the formation, or inhibit the growth of cyanobacteria or a cyanobacterial bloom. Blooms can occur in the open ocean, bays and lagoons, as well as freshwater environments. Nutrient enrichment of lakes, rivers and estuaries by urbanization (e.g., Fertilizer runoff or septic tank overflows) has led to increased incidence of cyanobacterial blooms. These blooms may produce toxic metabolites that are hazardous to public health and impact water quality, ecosystems, and drinking water supplies.

Examples of such phototrophs include, but are not limited to, cyanobacteria. Particular cyanobactia include, but are not limited to, *Anabaena* spp. (e.g., *Anabaena circinalis*, *Anabaena flos-aquae*), *Aphanizomenon* spp. (e.g., *Aphanizomenon flos-aquae*), *Aphanocapsa* spp., *Cylindrospermopsis* spp. (e.g., *Cylindrospermopsis raciborskii*), *Lyngbya* spp., *Merismopedia* spp., *Microcystis* spp. (e.g., *Microcystis aeruginosa*, *Microcystis viridis*, *Microcystis wesenbergii*), *Nodularia* spp. (e.g., *Nodularia harveyana*, *Nodularia spumigena*), *Nostoc* spp., *Oscillatoria* spp., *Planktothrix* spp., *Phormidium* spp. (e.g., *Phormidium tenue*), *Pseudanabaena* spp., *Raphidiopsis* spp., *Synechosystis* spp., *Synechococcus* spp., etc. See also U.S. Patent Publication No. 2009/0275018 to Neilan and U.S. Pat. No. 6,008,028 to Bender et al.

Other phototrophs include green algae (e.g., *Gloeocystis* spp.)

The water or aquatic system may be tested for the presence of cyanobacteria or their toxins, and/or visually observed for the presence of blooms. Toxins produced may include neurotoxins (e.g., anatoxin-a, anatoxin-a(s), saxitoxin, neosaxitoxin), hepatotoxins (e.g., microcystins, nodularins, cylindrospermopsin), and tumor promoting toxins (e.g., microcystins, lipopolysaccharides). Blooms may look like foam, scum, or mats on the surface of a body of water, and can be blue, green, brown or red. However, some blooms may not affect the appearance of the water.

Compounds may in some embodiments be applied to a body or water or aquatic system in combination with an algaecide as the microbicide and/or provided in a composition further comprising an algaecide as the microbicide, as detailed in the sections above. Microbicides may include those listed above and/or common aquatic microbicides such as chorine, choramine, bromine, copper or a salt or chelate thereof, silver, quats (quaternary ammonium salts), polyquats (polyalkyl quaternary amines such as benzalkonium chloride), or hydrogen peroxide.

Some aspects of the present disclosure are described in more detail in the following non-limiting examples.

Example 1

An 88-member library of compounds based upon the bacterial metabolite ethyl N-(2-phenethyl) carbamate (2d), isolated from the marine bacteria SCRC3P79 (*Cytophaga* sp.), was synthesized. It had been reported that 2d exhibited moderate antibiofilm activity against the marine α-proteobacteria *Rhodospirillum salexigens*. Yamada performed preliminary analogue synthesis by varying the aromatic appendage with substituted benzene rings and the ethyl appendage with a handful of aliphatic subunits. However, none of the analogues demonstrated improved activity in comparison to 2d (Yamada et al., *Bull. Chem. Soc. Jpn.*, 1997, 70, 3061).

Ethyl N-(2-phenethyl) carbamate 2d was synthesized from commercially available materials by routine acylation methodology (ethyl chloroformate/TEA in DCM) (Scheme 1). Compound 2d was isolated in 96% yield without recourse to chromatographic purification.

Scheme 1. Preparation of metabolite 2d and library design.

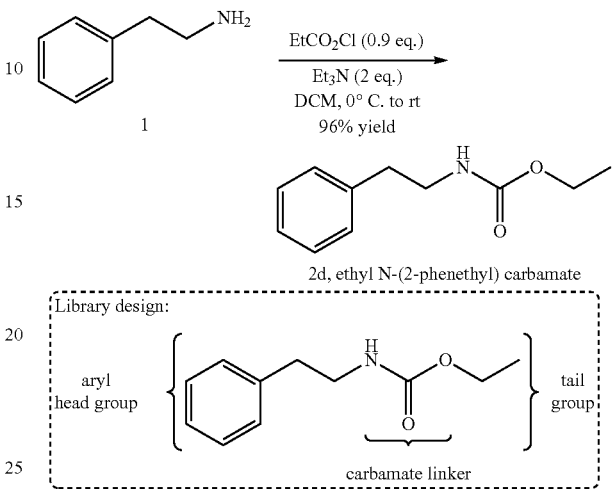

Similar to the results reported in Yamada et al., 2d displayed mediocre antibiofilm activity against *R. salexigens*, giving a 59.7% inhibition at a 200 μM concentration as judged by a crystal violet reporter assay (see O'Toole et al., *Mol. Microbiol.*, 1998, 30, 295).

Interestingly, we found that a 200 μM concentration of 2d also displayed activities against various medically relevant bacterial strains, inhibiting 63.1%, 68.1%, 80.2%, 52.0% and 40.8% of biofilm formation for *S. epidermidis*, methicillin-resistant *S. aureus* (MRSA), vancomycin-resistant *Enterococcus faecium* (VRE), multi-drug resistant *Acinetobacter baumannii* (MDRAB), and *E. coli* respectively (Table 1).

TABLE 1

Biofilm inhibition activity of 2d against various bacteria.

| Strain | % Inhibition (200 μM 2d) |
| --- | --- |
| S. epidermidis | 63.1 |
| MRSA | 68.1 |
| VRE | 80.2 |
| R. salexigens | 59.7 |
| MDRAB | 52.0 |
| E. coli | 40.8 |

Natural product analogues were synthesized using the same method used to prepare 2d. Specifically, the respective amine was reacted with 0.9 equivalent of the requisite chloroformate, isocyanate, dicarbonate, or isothiocyanate in the presence of 2.0 equivalents of triethylamine in dichloromethane. Each of the listed amines was reacted independently with each acylating reagent to produce the 88-member library in yields ranging from 76-98%.

Various aromatic head groups were used, incorporating the indole, triazole, indane, tetrahydroquinoline, indoline, and pyridine, as well as para-amino, para-methoxy, and para-bromo substituted phenyl rings. The carbamate heteroatomic core was varied through the substitution with a thiocarbamate, urea, and thiourea linkages. Tail modifications were made through the incorporation of the (-)-menthyl, benzyl, t-butyl and cholesteryl groups (Scheme 2).

Scheme 2. Analogue library.

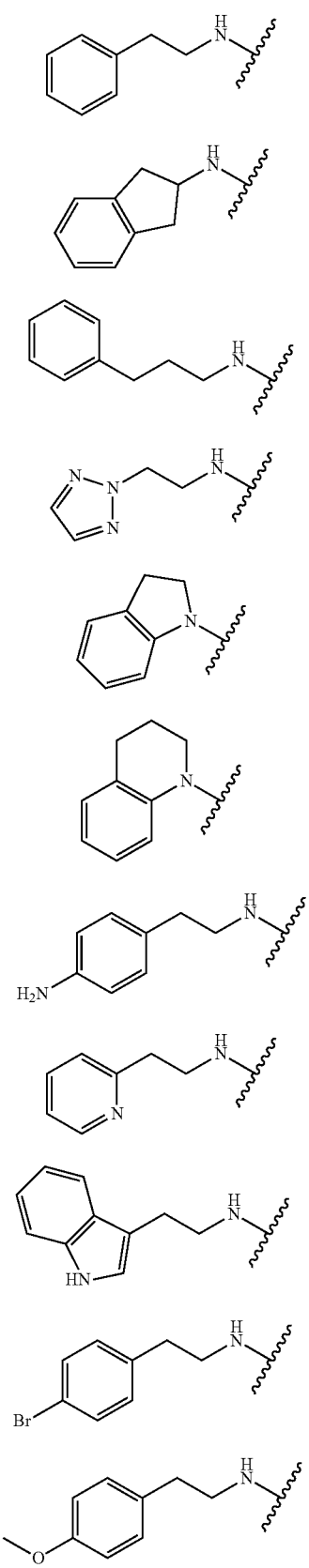

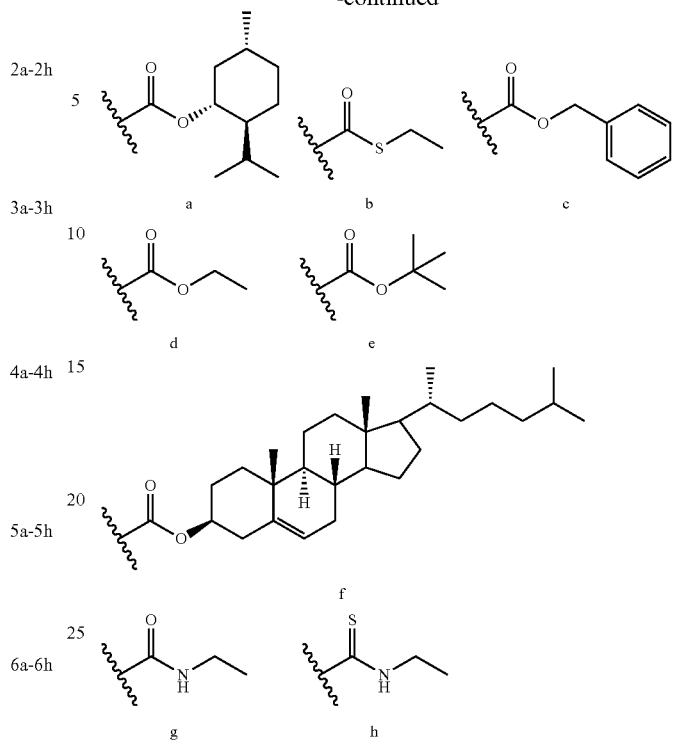

When these compounds were tested on *S. aureus* and MRSA strains, the most potent inhibitors had contained (−)-menthyl carbamates (Rogers et al., *Org. Biomol. Chem.*, 2010, 8(17):3857). Indeed, (−)-menthol and its derivatives have long been shown to have various antimicrobial and antiplasmid effects on bacteria (Schelz et al., *Fitoterapia*, 2006, 77, 279; Filoche et al., *Oral Microb. Immun.*, 2005, 20, 221; Iscan et al., *J. Agric. Food Chem.*, 2002, 50, 3943; Kurita et al. Agric. Biol. Chem., 1982, 46, 159; Aridogan et al., *Arch. Pharm. Res. Vol.* 2002, 25, 860). Along with (−)-menthol, the related natural products thymol (14) and carvacrol (15) (Scheme 3, dashed box) are also known to possess antimicrobial activity (Arfa et al., *Lett. Appl. Microbiol.*, 2006, 43, 149; Sivropoulou et al., *J. Agric. Food Chem.*, 1996, 44, 1202; Ultee et al., *J. Food Protect.*, 2000, 63, 620).

The thymyl and carvacryl carbamate analogues of 9a and 10a were also prepared because they had the lowest $IC_{50}$ values against MRSA and both worked well against 29213, 29740, and 25923 (see Tables 2 and 3). Additionally, the stereochemical antipodes of 9a and 10a were prepared by employing (+)-menthyl carbamate. Finally, the cyclohexyl carbamate derivatives of 9a and 10a were prepared as a control (Scheme 3).

Scheme 3. Analogues of compounds 9a and 10a.

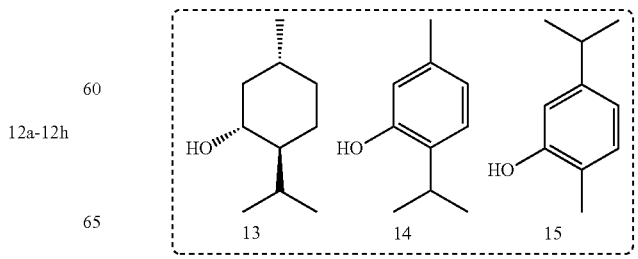

-continued

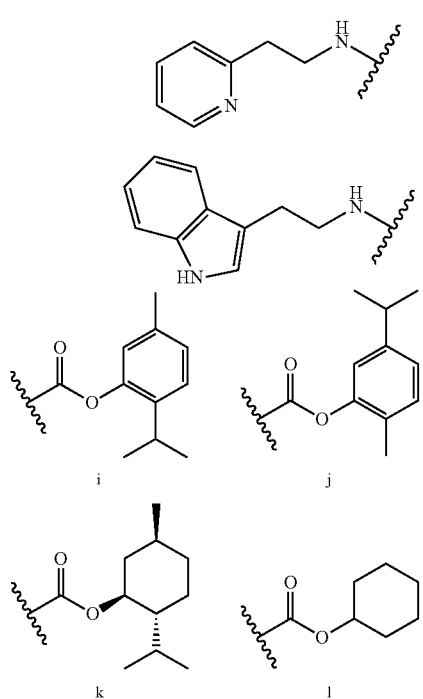

9i-9l 10i-10l i j k l

All reagents used for chemical synthesis were purchased from commercially available sources and used without further purification. Chromatography was performed using 60 Å mesh standard grade silica gel from Sorbtech. NMR solvents were obtained from Cambridge Isotope Labs and used as is. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. Mass spectra were obtained at the NCSU Department of Chemistry Mass Spectrometry Facility.

General Procedure for Compounds 2a-2h, 3a-3h, 4a-4h, 5a-5h, 6a-6h, 7a-7h, 11a-h and 12a-12h. Ten mL of dichloromethane and a stir bar was added to 100-200 mg of the amine. Two equivalents of triethylamine was then added and the reaction mixture was cooled to 0° C. while stirring. Then, 0.9 equivalents of the chloroformate, isocyanate or thioisocyanate was added dropwise to the reaction mixture and was allowed to slowly warm to room temperature and continued stirring overnight. The reaction mixture was then diluted with more dichloromethane, washed twice with 1N HCl, washed twice with brine, dried with sodium sulfate and then concentrated in vacuo.

General Procedure for Compounds 8a-8h, 9a-9l and 10a-10l. Ten mL of dichloromethane and a stir bar was added to 100-200 mg of the amine. Two equivalents of triethylamine was then added and the reaction mixture was cooled to 0° C. while stirring. Then, 0.9 equivalents of the chloroformate, isocyanate or thioisocyanate was added dropwise to the reaction mixture and was allowed to slowly warm to room temperature and continued stirring overnight. The reaction mixture was then diluted with more dichloromethane, washed twice with brine, dried with sodium sulfate and then concentrated in vacuo. The crude mixture was then purified via flash chromatography on silica gel using a 2.5%-10% methanol/dichlormethane eluent.

2-(2H-1,2,3-triazol-2-yl)ethanamine (5): White solid. mp=129-131° C. $^1$H NMR (300 MHz, CDCl$_3$) δ 7.43 (s, 2H), δ 4.55 (t, J=1.2 Hz, 2H), δ 3.33 (t, J=5.7 Hz, 2H) ppm; $^{13}$C NMR (75 MHz, CDCl$_3$) δ 135.1, 51.3, 38.8 ppm; IR ν$_{max}$ (cm$^{-1}$) 3054, 2987, 2306, 1421, 1258; HRMS (ESI) calcd for C$_4$H$_8$N$_4$(M+) 113.0822. found 113.0819.

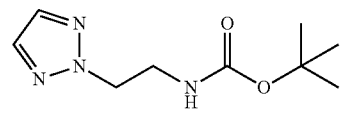

tert-butyl 2-(2H-1,2,3-triazol-2-yl)ethylcarbamate (5e): White solid. mp=64-66° C. $^1$H NMR (300 MHz, CDCl$_3$) δ 7.55 (s, 2H), δ 5.15 (s, 1H), δ 4.49 (t, J=5.7 Hz, 2H), δ 3.63 (q, J=5.7, 5.1 Hz, 2H), δ 1.36 (s, 9H) ppm; $^{13}$C NMR (75 MHz, CDCl$_3$) δ 155.9, 134.5, 79.8, 54.8, 40.2, 28.5, 27.8 ppm; IR ν$_{max}$ (cm$^{-1}$) 3054, 2986, 1713, 1506; HRMS (ESI) calcd for C$_9$H$_{16}$N$_4$O$_2$ (M+) 235.1165. found 235.1169.

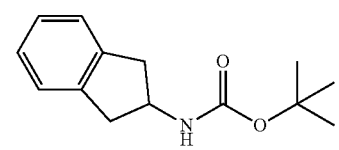 [SMILES: CC(C)(C)OC(=O)NC1Cc2ccccc2C1]

tert-butyl 2,3-dihydro-1H-inden-2-ylcarbamate (3e): White solid. mp=51-53° C. $^1$H NMR (300 MHz, CDCl$_3$) δ 7.19 (m, 4H), δ 4.84 (s, 1H), δ 4.45 (s, 1H), δ 3.29 (d, J=7.2 Hz, 1H), δ 3.24 (d, J=6.9 Hz, 1H), δ 2.80 (d, J=4.8 Hz, 1H), δ 2.75 (d, J=4.8 Hz, 1H), δ 1.43 (s, 9H) ppm; $^{13}$C NMR (75 MHz, CDCl$_3$) δ 153.5, 140.9, 126.5, 124.7, 79.3, 51.9, 40.3, 28.4 ppm; IR ν$_{max}$ (cm$^{-1}$) 3419, 2321, 1641; HRMS (ESI) calcd for C$_{17}$H$_{17}$NO$_2$ (M+) 256.1308. found 256.1308.

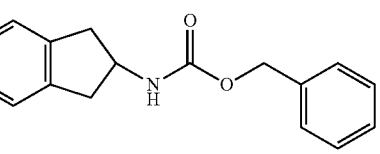

benzyl 2,3-dihydro-1H-inden-2-ylcarbamate (3c): Light yellow solid. mp=159-161° C. $^1$H NMR (300 MHz, CDCl$_3$) δ 7.35 (s, 4H), δ 7.13 (t, J=1.2 Hz, 5H), δ 5.09 (s, 2H), δ 4.56 (s, 2H), δ 3.28 (m, 2H), δ 2.77 (m, 2H) ppm; $^{13}$C NMR (75 MHz, CDCl$_3$) δ 141.3, 136.7, 128.8, 126.9, 125.0, 66.9, 51.8, 40.8 ppm; IR ν$_{max}$ (cm$^{-1}$) 3419, 2977, 1691, 1643, 1265; HRMS (ESI) calcd for C$_{17}$H$_{17}$NO$_2$(M+) 268.1332. found 268.1337.

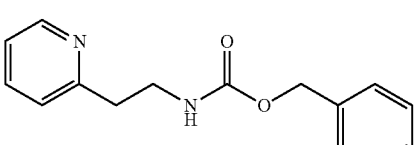

benzyl 2-(pyridin-2-yl)ethylcarbamate (9c): Colorless oil. ¹H NMR (300 MHz, CDCl₃) δ 8.43 (d, J=4.8 Hz, 1H), δ 7.52 (t, J=1.8 Hz, 1H), δ 7.23 (s, 5H), δ 7.06 (m, 2H), δ 5.91 (s, 1H), δ 5.04 (s, 2H), δ 3.57 (q, J=6.3 Hz, 2H), δ 2.93 (t, J=6.6 Hz, 2H) ppm; ¹³C NMR (75 MHz, CDCl₃) δ 156.7, 149.4, 137.0, 128.6, 127.1, 123.7, 121.7, 66.7, 40.6, 37.8 ppm; 3440, 2092, 1644, 1261; HRMS (ESI) calcd for C₁₅H₁₆N₂O₂(M+) 257.1285. found 257.1288.

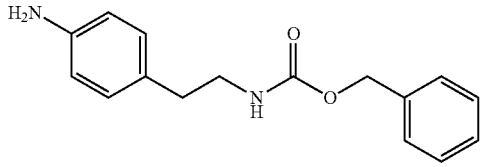 [SMILES: Nc1ccc(CCNC(=O)OCc2ccccc2)cc1]

benzyl 4-aminophenethylcarbamate (8c): Light yellow solid. mp=70-73° C. ¹H NMR (300 MHz, CDCl₃) δ 7.31 (s, 5H), δ 6.93 (d, J=8.1 Hz, 2H), δ 6.58 (d, J=8.4 Hz, 2H), δ 5.06 (s, 2H), δ 4.91 (s, 1H), δ 3.57 (s, 2H), δ 3.36 (q, J=6.6, 6.6 Hz, 2H), δ 2.65 (t, J=6.9 Hz, 2H) ppm; ¹³C NMR (75 MHz, CDCl₃) δ 156.6, 145.2, 136.9, 129.8, 128.7, 115.6, 66.8, 58.8, 42.7, 35.4 ppm; IR ν$_{max}$ (cm⁻¹) 3389, 1682, 1543; HRMS (ESI) calcd for C₁₆H₁₈N₂O₂ (M+) 271.1441. found 271.1446.

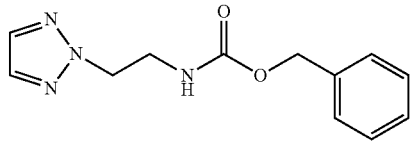 [SMILES: O=C(NCCn1nccn1)OCc1ccccc1]

benzyl 2-(2H-1,2,3-triazol-2-yl)ethylcarbamate (5c): Light yellow residue. ¹H NMR (300 MHz, CDCl₃) δ 7.58 (s, 2H), δ 7.28 (m, 5H), δ 5.38 (s, 1H), δ 5.15 (s, 2H), δ 4.51 (t, J=5.4 Hz, 2H), δ 3.75 (t, J=6.3 Hz, 2H) ppm; ¹³C NMR (75 MHz, CDCl₃) δ 156.5, 136.5, 134.5, 128.4, 67.1, 54.6, 40.6 ppm; IR ν$_{max}$ (cm⁻¹) 3440, 3054, 2986, 2305, 1719; HRMS (ESI) calcd for C₁₂H₄N₄O₂ (M+) 269.1009. found 269.1011.

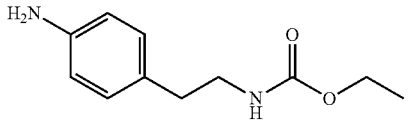

ethyl 4-aminophenethylcarbamate (8d): Light yellow oil. ¹H NMR (300 MHz, CDCl₃) δ 6.95 (d, J=8.1 Hz, 2H), δ 6.61 (d, J=6.3 Hz, 2H), δ 4.89 (s, 1H), δ 4.08 (q, J=6.9, 7.2 Hz, 2H), δ 3.74 (s, 2H), δ 3.33 (t, J=6.3 Hz, 2H), δ 2.65 (t, J=7.2 Hz, 2H), δ 1.19 (t, J=7.2 Hz, 3H) ppm; ¹³C NMR (75 MHz, CDCl₃) δ 156.9, 145.0, 129.8, 115.7, 60.9, 42.6, 35.4, 14.9 ppm; IR ν$_{max}$ (cm⁻¹) 3346, 2932, 1698, 1627; HRMS (ESI) calcd for C₁₁H₁₆N₂O₂ (M+) 209.1285. found 209.1278.

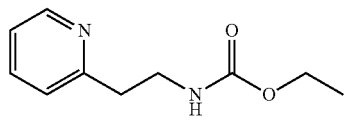

ethyl 2-(pyridin-2-yl)ethylcarbamate (9d): Light yellow solid. mp=56-58° C. ¹H NMR (300 MHz, CDCl₃) δ 8.41 (d, J=4.8 Hz, 1H), δ 7.49 (t, J=5.7 Hz, 1H), δ 7.02 (m, 2H), δ 5.77 (s, 1H), δ 4.00 (q, J=6.9, 7.2 Hz, 2H), δ 3.50 (q, J=6.3, 6.6 Hz, 2H), δ 2.89 (t, J=6.6 Hz, 2H), δ 1.11 (t, J=6.9 Hz, 3H) ppm; ¹³C NMR (75 MHz, CDCl₃) δ 159.5, 156.9, 149.3, 136.6, 123.5, 121.6, 60.6, 40.4, 37.9, 14.8 ppm; IR ν$_{max}$ (cm⁻¹) 3435, 2091, 1641, 1259; HRMS (ESI) calcd for C₁₄H₁₇N₅O₂S (M+). found.

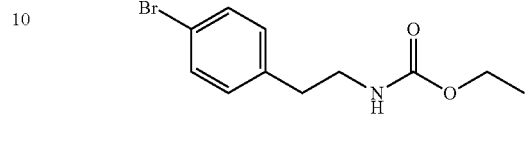

ethyl 4-bromophenethylcarbamate (11d): White solid. mp=63-65° C. ¹H NMR (300 MHz, CDCl₃) δ 7.42 (d, J=2.7 Hz, 2H), δ 7.07 (d, J=8.7 Hz, 2H), δ 4.94 (s, 1H), δ 4.09 (q, J=6.9, 7.2 Hz, 2H), δ 3.39 (q, J=6.6, 6.9 Hz, 2H), δ 2.75 (t, 6.9 Hz, 2H), δ 1.21 (t, J=7.2 Hz, 3H) ppm; ¹³C NMR (75 MHz, CDCl₃) δ 156.8, 138.1, 131.7, 120.5, 61.0, 42.1, 35.8, 14.9 ppm; IR ν$_{max}$ (cm⁻¹) 3348, 2975, 1691, 1537, 1260; HRMS (ESI) calcd for C₁₁H₁₄BrNO₂(M+) 227.0281. found 227.0279.

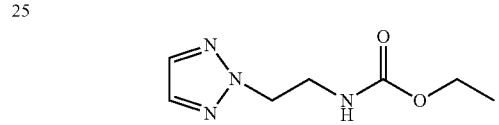

ethyl 2-(2H-1,2,3-triazol-2-yl)ethylcarbamate (5d): Colorless oil. ¹H NMR (300 MHz, CDCl₃) δ 7.62 (s, 2H), δ 6.31 (s, 1H), δ 4.671 (t, J=4.2 Hz, 2H), δ 4.17 (q, J=4.5, 4.5 Hz, 2H), δ 3.31 (s, 2H), δ 1.21 (t, J=6.9 Hz, 3H) ppm; ¹³C NMR (75 MHz, CDCl₃) δ 202.1, 134.7, 54.2, 44.3, 41.8, 14.1 ppm; IR ν$_{max}$ (cm⁻¹) 3434, 1642; HRMS (ESI) calcd for C₁₄H₁₇N₅O₂S (M+). found.

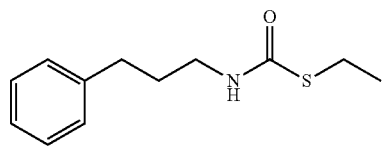

S-ethyl 3-phenylpropylcarbamothioate (4b): Colorless oil. ¹H NMR (300 MHz, CDCl₃) δ 7.25-7.10 (m, 5H), δ 6.24 (s, 1H), 3.26 (t, J=5.7 Hz, 2H), δ 2.82 (q, J=4.8, 6.9 Hz, 2H), δ 2.58 (t, J=7.8 Hz, 2H), δ 1.76 (m, 2H), δ 1.26 (t, J=7.5 Hz, 3H) ppm; ¹³C NMR (75 MHz, CDCl₃) δ 137.8, 141.7, 128.7, 126.5, 41.3, 33.4, 32.0, 24.5, 16.1 ppm; IR ν$_{max}$ (cm⁻¹) 3318, 3027, 2929, 2867, 1650, 1624, 1215, 700; HRMS (ESI) calcd for C₁₂H₁₇NOS (M+) 224.1104. found 224.1099.

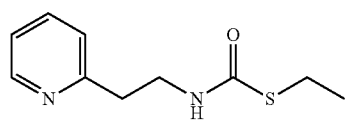

S-ethyl 2-(pyridin-2-yl)ethylcarbamothioate (9b): Colorless oil. ¹H NMR (300 MHz, CDCl₃) δ 8.37 (d, J=3 Hz, 1H), δ 7.47 (t, J=6.0 Hz, 1H), δ 7.01 (m, 2H), δ 6.88 (s, 1H), δ 3.58 (q, J=4.8, 4.5, 2 H), 2.89 (t, J=5.1 Hz, 2H), δ 2.78 (q, J=5.4, 5.4 Hz, 2H), δ 1.15 (t, J=5.1 Hz, 3H) ppm; ¹³C NMR (75 MHz, CDCl$_3$) δ 159.3, 149.3, 136.8, 123.6, 121.8, 40.7, 37.4, 24.6, 15.9 ppm; IR ν$_{max}$ (cm$^{-1}$) 3432, 2089, 1645, 1213; HRMS (ESI) calcd for C$_{14}$H$_{17}$N$_5$O$_2$S (M+). found.

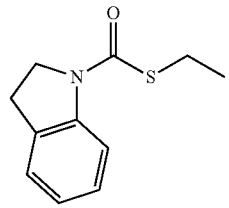

S-ethyl indoline-1-carbothioate (6b): Light yellow oil. $^1$H NMR (300 MHz, CDCl$_3$) δ 7.97 (d, J=5.7 Hz, 1H), 7.08-6.88 (m, 4H), δ 3.80 (t, J=7.8 Hz, 2H), 2.94 (q, J=6.0, 5.4 Hz, 2H), δ 2.89 (t, J=3.3 Hz, 2H), δ 1.31 (t, J=5.7 Hz, 3H) ppm; $^{13}$C NMR (75 MHz, CDCl$_3$) 165.6, 143.0, 131.3, 127.6, 124.9, 123.6, 116.0, 47.3, 28.0, 24.7, 15.7 ppm; IR ν$_{max}$ (cm$^{-1}$) 3053, 2932, 2253, 1712, 1598, 1650; HRMS (ESI) calcd for C$_{11}$H$_{13}$NOS (M+) 208.0791. found 208.0788.

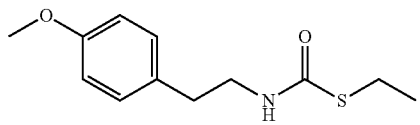 [SMILES: CCSC(=O)NCCc1ccc(OC)cc1]

S-ethyl 4-methoxyphenethylcarbamothioate (12b): Colorless oil. $^1$H NMR (300 MHz, CDCl$_3$) δ 7.09 (d, J=8.4 Hz, 2H), δ 6.83 (d, J=8.7, 2 H), δ 5.96 (s, 1H), δ 3.50 (s, 3H), δ 3.45 (q, J=6.3, 6.6 Hz, 2H), δ 2.91 (q, J=3.3, 3.3 Hz, 2H), δ 2.75 (t, J=7.5 Hz, 2H), δ 1.28 (t, J=6.9 Hz, 3H) ppm; $^{13}$C NMR (75 MHz, CDCl$_3$) δ 167.7, 158.5, 130.9, 129.9, 114.2, 55.4, 43.0, 35.2, 24.4, 16.0 ppm; IR ν$_{max}$ (cm$^{-1}$) 3323, 3034, 2962, 1640, 1514; HRMS (ESI) calcd for C$_{14}$H$_{17}$N$_5$O$_2$S (M+). found.

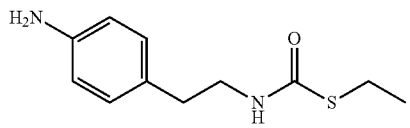

S-ethyl 4-aminophenethylcarbamothioate (8b): Light yellow oil. $^1$H NMR (400 MHz, CDCl$_3$) δ 6.92 (d, J=6.8, 2 H), δ 6.59 (t, J=6.4 Hz, 2H), δ 5.87 (s, 1H), S 3.77 (s, 1H), δ 3.41 (t, J=5.6 Hz, 2H), δ 2.86 (q, J=7.2, 7.2 Hz, 2H), δ 2.67 (t, J=6.4, 2 H), S 1.25 (t, J=5.2 Hz, 3H) ppm; $^{13}$C NMR (100 MHz, CDCl$_3$) δ 167.6, 145.1, 129.8, 115.7, 53.8, 43.0, 35.2, 24.5, 16.0 ppm; IR ν$_{max}$ (cm$^{-1}$) 3434, 2929, 2086, 1647, 1517, 1263, 1219, 970; HRMS (ESI) calcd for C$_{11}$H$_{16}$N$_2$OS (M+) 225.1056. found 225.1060.

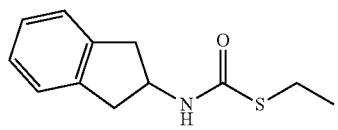

S-ethyl 2,3-dihydro-1H-inden-2-ylcarbamothioate (3b): White solid. mp=107-110° C. $^1$H NMR (300 MHz, CDCl$_3$) δ 7.23-7.15 (m, 4H), δ 6.08 (d, J=5.4 Hz, 1H), δ 4.70 (s, 1H), δ 3.26 (dd, J=7.2, 7.2 Hz, 2H), δ 2.86 (q, J=5.4, 6.6 Hz, 2H), δ 1.29 (t, J=7.5 Hz, 3H) ppm; $^{13}$C NMR (75 MHz, CDCl$_3$) δ 167.4, 141.0, 127.1, 125.0, 52.7, 40.2, 24.5, 16.0 ppm; IR ν$_{max}$ (cm$^{-1}$) 3258, 3019, 2945, 1628; HRMS (ESI) calcd for C$_{12}$H$_{15}$NOS (M+) 222.0947. found 222.0944.

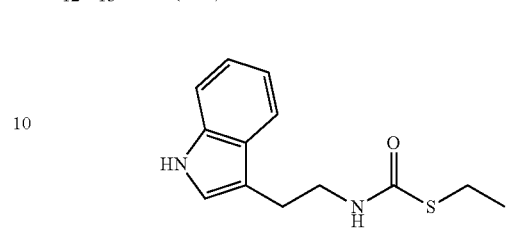

S-ethyl 2-(1H-indol-3-yl)ethylcarbamothioate (10b): Light yellow solid. mp=68-70° C. $^1$H NMR (300 MHz, CDCl$_3$) δ 8.52 (s, 1H), δ 7.54 (d, J=7.8, 1 H), δ 7.24 (d, J=8.1, 1 H), δ 7.17-7.04 (m, 2H), δ 6.82 (d, J=2.1 Hz, 1H), δ 5.74 (s, 1H), δ 3.51 (t, J=6.3 Hz, 2H), δ 2.91-2.83 (m, 4H), δ 1.26 (t, J=4.5 Hz, 3H) ppm; $^{13}$C NMR (75 MHz, CDCl$_3$) δ 168.2, 136.8, 127.6, 122.8, 119.7, 112.6, 42.1, 25.8, 24.7, 16.2 ppm; IR ν$_{max}$ (cm$^{-1}$) 3418, 3055, 2932, 1657, 1496; HRMS (ESI) calcd for C$_{13}$H$_{16}$N$_2$OS (M+) 249.1056. found 249.1052.

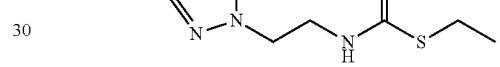

S-ethyl 2-(2H-1,2,3-triazol-2-yl)ethylcarbamothioate (5b): Colorless oil. $^1$H NMR (300 MHz, CDCl$_3$) δ 7.59 (s, 1H), δ 6.14 (s, 1H), δ 4.56 (t, J=5.1 Hz, 2H), δ 3.83 (q, J=5.7, 5.7 Hz, 2H), δ 2.88 (q, J=7.5, 7.5 Hz, 2H), δ 1.25 (t, J=7.5 Hz, 3H) ppm; $^{13}$C NMR (75 MHz, CDCl$_3$) δ 202.1, 134.7, 54.3, 40.5, 24.6, 15.8 ppm; IR ν$_{max}$ (cm$^{-1}$) 3434, 1647, 671; HRMS (ESI) calcd for C$_{14}$H$_{17}$N$_5$O$_2$S (M+). found.

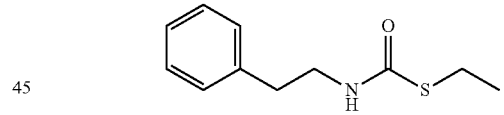

S-ethyl phenethylcarbamothioate (2b): White solid. mp=95-98° C. $^1$H NMR (300 MHz, CDCl$_3$) δ 7.30 (m, 5H), δ 6.02 (s, 1H), δ 3.53 (q, J=6.6, 6.6 Hz, 2H), δ 2.89 (m, 4H), δ 1.30 (t, J=6.6 Hz, 3H) ppm; $^{13}$C NMR (75 MHz, CDCl$_3$) δ 167.8, 139.0, 129.1, 126.8, 42.9, 36.2, 24.5, 16.1 ppm; IR ν$_{max}$ (cm$^{-1}$) 3399, 2968, 2929, 2870, 2088, 1650, 1498; HRMS (ESI) calcd for C$_{11}$H$_{15}$NOS (M+) 210.0947. found 210.0944.

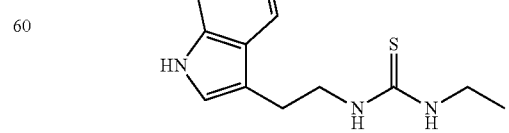

1-(2-(1H-indol-3-yl)ethyl)-3-ethylthiourea (10h): Light yellow residue. $^1$H NMR (300 MHz, CDCl$_3$) δ 8.67 (s, 1H), δ 7.58 (d, J=7.2 Hz, 1H), δ 7.33 (d, J=8.1 Hz, 1H), δ 7.18 (t, J=6.9 Hz, 1H), δ 7.08 (t, J=7.2 Hz, 1H), δ 6.86 (s, 1H), δ 6.24 (s, 2H), δ 3.69-2.94 (m, 6H), δ 1.00 (t, J=6.9 Hz, 3H) ppm; $^{13}$C NMR (75 MHz, CDCl$_3$) δ 180.9, 136.7, 127.4, 122.4, 118.9, 112.3, 45.0, 39.4, 25.3, 14.4 ppm; IR ν$_{max}$ (cm$^{-1}$) 3418, 2975, 1634, 1569, 1265, 738, 702; HRMS (ESI) calcd for C$_{13}$H$_{17}$N$_3$S (M+) 248.1216. found 248.1215.

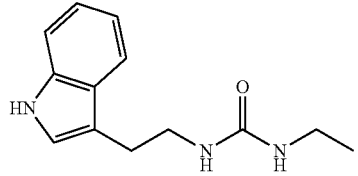 [SMILES: CCSC(=O)NCCc1c[nH]c2ccccc12]

1-(2-(1H-indol-3-yl)ethyl)-3-ethylurea (10g): White solid. mp=109-112° C. $^1$H NMR (300 MHz, CDCl$_3$) δ 8.55 (s, 1H), δ 7.57 (d, J=7.8 Hz, 1H), δ 7.32-7.05 (m, 3H), δ 6.86 (s, 1H), δ 6.13 (s, 2H), δ 3.69 (m, 2H), δ 3.20 (m, 2H), δ 2.94 (t, J=6.3 Hz, 2H), δ 0.97 (t, J=7.2 Hz, 3H) 181.0, 136.6, 127.4, 122.9, 119.7, 112.3, 44.6, 39.0, 25.2, 14.3 ppm; $^{13}$C NMR (75 MHz, CDCl$_3$) δ 180.9, 136.6, 127.4, 122.9, 122.4, 119.7, 112.3, 111.9, 44.6, 38.9, 25.2, 14.4 ppm; IR ν$_{max}$ (cm$^{-1}$) 3944, 3467, 3054, 2986, 2306, 1536; HRMS (ESI) calcd for C$_{13}$H$_{17}$N$_3$O (M+) 232.1444. found 232.1445.

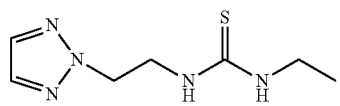

1-(2-(2H-1,2,3-triazol-2-yl)ethyl)-3-ethylthiourea (5h): White solid. mp=91-93° C. $^1$H NMR (300 MHz, CDCl$_3$) δ 7.57 (d, J=9.6 Hz 2H), δ 6.64 (s, 2H), δ 4.62 (q, J=5.1, 3.9 Hz, 2H), δ 4.10 (q, J=5.7, 5.4 Hz), δ 3.28 (t, J=5.7 Hz, 2H), δ 1.15 (t, J=9.3 Hz, 3H) ppm; $^{13}$C NMR (75 MHz, CDCl$_3$) δ 197.1, 134.7, 100.4, 54.1, 44.2, 14.1 ppm; IR ν$_{max}$ (cm$^{-1}$) 3419, 1640, 1551; HRMS (ESI) calcd for C$_{14}$H$_{17}$N$_5$O$_2$S (M+). found.

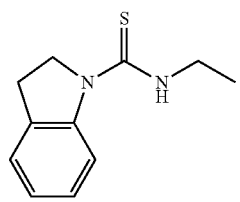

N-ethylindoline-1-carbothioamide (6h): Yellow solid. mp=88-91° C. $^1$H NMR (300 MHz, CDCl$_3$) δ 7.83 (d, J=7.8 Hz, 2H), S 7.08-7.01 (m, 2H), δ 6.85 (t, J=7.2 Hz, 1H), δ 6.21 (t, J=4.5 Hz, 1H), δ 4.09 (t, J=8.4 Hz, 2H), δ 3.63 (m, 2H), δ 2.87 (t, J=8.4 Hz, 2H), δ 1.18 (t, J=7.2 Hz, 3H) ppm; $^{13}$C NMR (75 MHz, CDCl$_3$) δ 178.9, 142.5, 134.0, 127.1, 125.9, 123.4, 114.9, 53.4, 40.3, 27.3, 14.6 ppm; IR ν$_{max}$ (cm$^{-1}$) 3390, 3279, 3030, 2972, 1638, 1522; HRMS (ESI) calcd for C$_{11}$H$_{14}$N$_2$S (M+) 207.0950. found 207.0946.

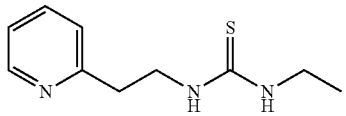

1-ethyl-3-(2-(pyridin-2-yl)ethyl)thiourea (9h): Light yellow oil. $^1$H NMR (300 MHz, CDCl$_3$) δ 8.25 (d, J=4.2 Hz, 1H), δ 7.43 (t, J=7.5 Hz, 1H), δ 7.33 (s, 1H), δ 7.01-6.92 (m, 3H), δ 3.70 (t, J=3.9 Hz, 2H), δ 3.21 (m, 2H), δ 2.85 (t, J=6.3 Hz, 2H), δ 0.98 (t, J=6.9 Hz, 3H) ppm; $^{13}$C NMR (75 MHz, CDCl$_3$) δ 202.3, 181.0, 159.4, 150.0, 148.9, 137.1, 123.8, 121.9, 43.8, 39.0, 36.8, 24.7, 14.3 ppm; IR ν$_{max}$ (cm$^{-1}$) 3396, 2974, 2100, 1641, 1556; HRMS (ESI) calcd for C$_{14}$H$_{17}$N$_5$O$_2$S (M+). found.

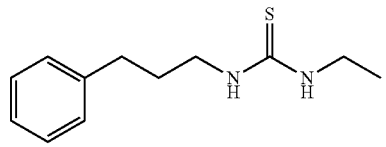

1-ethyl-3-(3-phenylpropyl)thiourea (4h) White solid. mp=51-53° C. $^1$H NMR (300 MHz, CDCl$_3$) δ 7.25-7.11 (m, 5H), δ 6.42 (s, 2H), δ 3.42 (m, 2H), δ 3.34 (m, 2H), δ 2.61 (t, J=7.5 Hz, 2H), δ 1.86 (m, 2H), 1.10 (t, J=7.2 Hz, 3H) ppm; $^{13}$C NMR (75 MHz, CDCl$_3$) δ 181.3, 141.4, 128.7, 126.3, 39.3, 33.9, 30.8, 14.6 ppm; IR ν$_{max}$ (cm$^{-1}$) 3421, 3276, 3053, 2939, 2865, 1547, 1495; HRMS (ESI) calcd for C$_{12}$H$_{18}$N$_2$S (M+) 223.1263. found 223.1261.

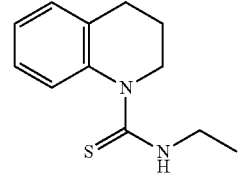

N-ethyl-3,4-dihydroquinoline-1(2H)-carbothioamide (7h): Light yellow solid. mp=55-57° C. $^1$H NMR (300 MHz, CDCl$_3$) δ 7.09-6.97 (m, 4H), δ 6.22 (s, 1H), δ 4.09 (t, J=6.3 Hz, 2H), δ 3.50 (m, 2H), δ 2.59 (t, J=6.9 Hz, 2H), δ 1.84 (m, 2H), δ 1.02 (t, J=3.9 Hz, 3H) ppm; $^{13}$C NMR (75 MHz, CDCl$_3$) δ 181.9, 138.8, 134.0, 130.3, 126.8, 123.7, 49.1, 40.9, 26.7, 24.0, 14.3 ppm; IR ν$_{max}$ (cm$^{-1}$) 3396, 3034, 2934, 2875, 2211, 1640, 1516; HRMS (ESI) calcd for C$_{12}$H$_{16}$N$_2$S (M+) 221.1107. found 221.1105.

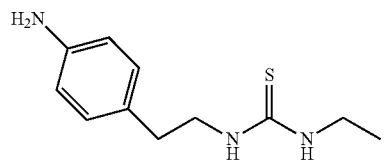

1-(4-aminophenethyl)-3-ethylthiourea (8h): Light yellow oil. $^1$H NMR (300 MHz, CDCl$_3$) δ 6.94 (d, J=8.1, 2 H), δ 6.57 (d, J=4.5 Hz, 2H), δ 6.06 (d, J=10.2 Hz, 2H), δ 3.60 (m, 4H), δ 3.26 (s, 2H), δ 2.72 (t, J=6.9 Hz, 2H), δ 1.08 (t, J=7.2 Hz, 3H) ppm; $^{13}$C NMR (75 MHz, CDCl$_3$) δ 181.3, 145.3, 129.8, 128.3, 115.7, 46.1, 39.1, 34.6, 14.4 ppm; IR $v_{max}$ (cm$^{-1}$) 3408, 1626, 1553; HRMS (ESI) calcd for C$_{11}$H$_{17}$N$_3$S (M+) 224.1216. found 224.1212.

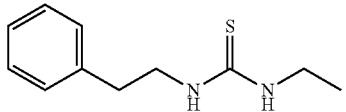

1-ethyl-3-phenethylthiourea (2h): White solid. mp=56-58° C. $^1$H NMR (300 MHz, CDCl$_3$) δ 7.27-7.14 (m, 5H), δ 6.40 (d, J=10.2 Hz, 2H), δ 3.68 (t, J=5.1 Hz, 2H), δ 3.30 (m, 2H), δ 2.84 (t, J=7.2 Hz, 2H), δ 1.08 (t, J=7.2 Hz, 3H) ppm; $^{13}$C NMR (75 MHz, CDCl$_3$) 181.4, 138.7, 129.0, 126.9, 45.9, 39.1, 35.6, 14.4 ppm; IR $v_{max}$ (cm$^{-1}$) 3420, 3269, 3054, 2984, 2935, 2875, 2685, 2306, 2253, 1711, 1546; HRMS (ESI) calcd for C$_{11}$H$_{16}$N$_2$S (M+) 209.1107. found 209.1103.

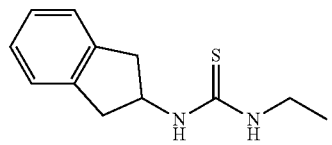

1-(2,3-dihydro-1H-inden-2-yl)-3-ethylthiourea (3h): Grey solid. mp=87-91° C. $^1$H NMR (300 MHz, CDCl$_3$) δ 7.14 (m, 4H), δ 6.62 (s, 2H), δ 4.85 (m, 1H), δ 3.50-3.21 (m, 4H), δ 2.83 (dd, J=5.4, 5.1 Hz, 2H), δ 1.10 (t, J=7.5 Hz, 3H) ppm; $^{13}$C NMR (75 MHz, CDCl$_3$) δ 181.0, 140.8, 127.1, 125.0, 100.4, 55.5, 40.0, 14.6 ppm; IR $v_{max}$ (cm$^{-1}$) 3267, 3066, 2972, 1673, 1483, 1548; HRMS (ESI) calcd for C12H$_{16}$N$_2$S (M+) 221.1107. found 221.1106.

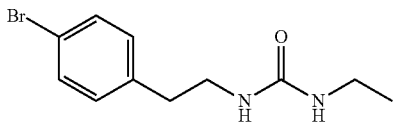

1-(4-bromophenethyl)-3-ethylurea (11g): White solid. mp=137-139° C. $^1$H NMR (300 MHz, CDCl$_3$) δ 7.37 (d, J=8.1 Hz, 2H), δ 7.02 (d, J=8.1 Hz, 2H), δ 5.46 (d, J=16.5 Hz, 2H), δ 3.30 (m, 2H), δ 3.08 (q, J=6.0, 6.9 Hz, 2H), δ 2.67 (t, J=6.9 Hz, 2H), δ 1.05 (t, J=7.2 Hz, 3H) ppm; $^{13}$C NMR (75 MHz, CDCl$_3$) δ 159.1, 138.6, 131.7, 130.7, 120.3, 41.6, 36.3, 35.2, 15.8 ppm; IR $v_{max}$ (cm$^{-1}$) 3327, 2971, 1620, 1488; HRMS (ESI) calcd for C$_{11}$H$_{15}$BrN$_2$O (M+) 271.0441. found 271.0439.

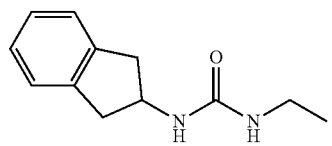

1-(2,3-dihydro-1H-inden-2-yl)-3-ethylurea (3g): White solid. mp=117° C. $^1$H NMR (300 MHz, CDCl$_3$) δ 7.14 (m, 4H), δ 5.98 (s, 2H), δ 4.43 (m, 1H), δ 3.22-3.07 (m, 4H), δ 2.77 (dd, J=6.3, 5.7 Hz, 2H), δ 1.07 (t, J=6.9 Hz, 3H) ppm; $^{13}$C NMR (75 MHz, CDCl$_3$) δ 159.3, 141.4, 126.8, 124.9, 51.5, 40.7, 35.1, 15.9 ppm; IR $v_{max}$ (cm$^{-1}$) 3348, 2968, 1623, 1579, 1259, 736; HRMS (ESI) calcd for C$_{12}$H$_{16}$N$_2$O (M+) 205.1335. found 205.1333.

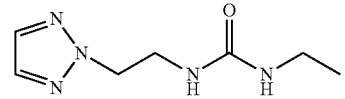

1-(2-(2H-1,2,3-triazol-2-yl)ethyl)-3-ethylurea (5g): White solid. mp=109° C. $^1$H NMR (300 MHz, CDCl$_3$) δ 7.57 (s, 2H), δ 6.63 (d, J=25.5 Hz, 2H), δ 4.62 (m, 2H), δ 4.10 (t, J=5.1 Hz, 2H), δ 3.28 (m, 2H), δ 1.16 (t, J=8.7 Hz, 3H) ppm; $^{13}$C NMR (75 MHz, CDCl$_3$) δ 174.6, 134.7, 54.3, 44.2, 38.7, 14.1 ppm; IR $v_{max}$ (cm$^{-1}$) 3434, 1640; HRMS (ESI) calcd for C$_7$H$_{13}$N$_5$O (M+) 206.1012. found 206.1014.

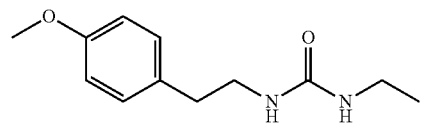 [SMILES: CCNC(=O)NCCc1ccc(OC)cc1]

1-ethyl-3-(4-methoxyphenethyl)urea (12g): Light yellow oil. $^1$H NMR (300 MHz, CDCl$_3$) δ 7.03 (d, J=8.7 Hz, 2H), δ 6.78 (t, J=3.9 Hz, 2H), 5.85 (q, J=5.1, 6.3 Hz, 2H), δ 3.73 (s, 3H), δ 3.31 (q, J=6.6, 7.2 Hz, 2H), δ 3.12 (m, 2H), δ 2.67 (t, J=7.5 Hz, 2H), δ 1.08 (t, J=7.2 Hz, 3H) ppm; $^{13}$C NMR (75 MHz, CDCl$_3$) δ 159.6, 158.3, 131.7, 129.9, 114.1, 55.4, 42.1, 36.1, 35.1, 15.8 ppm; IR $v_{max}$ (cm$^{-1}$) 3374, 2977, 2837, 1630; HRMS (ESI) calcd for C$_{12}$H$_{18}$N$_2$O$_2$ (M+) 245.1260. found 245.1263.

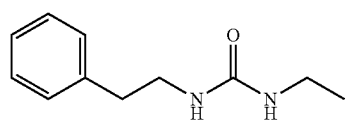

1-ethyl-3-phenethylurea (2g): White solid. mp=75-77° C. $^1$H NMR (300 MHz, CDCl$_3$) 7.22 (m, 5H), δ 5.92 (d, J=16.2 Hz, 2H), δ 3.86 (q, J=6.6, 6.0 Hz, 2H), δ 3.14 (m, 2H), δ 2.78 (t, J=7.8 Hz, 2H), δ 1.10 (t, J=7.2 Hz, 3H) ppm; $^{13}$C NMR (75 MHz, CDCl$_3$) δ 159.6, 139.7, 129.0, 126.5, 41.9, 37.1, 35.1, 15.9 ppm; IR $v_{max}$ (cm$^{-1}$) 3359, 2972, 2873, 2239, 1633, 1259; HRMS (ESI) calcd for C$_{11}$H$_{16}$N$_2$O (M+) 193.1335. found 193.1334.

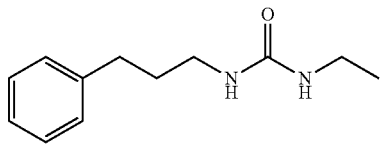

1-ethyl-3-(3-phenylpropyl)urea (4g): White solid. mp=48° C. $^1$H NMR (300 MHz, CDCl$_3$) δ 7.2 (m, 5H), δ 6.15 (s, 1H), δ 6.08 (s, 1H), δ 3.26 (m, 4H), δ 2.69 (t, J=9 Hz, 2H), δ 1.84 (m, 2H), δ 1.14 (t, J=7.5 Hz, 3H) ppm; $^{13}$C NMR (75 MHz, CDCl$_3$) δ 160.0, 142.0, 128.6, 126.1, 40.0, 35.2, 33.5, 32.4, 15.9 ppm; IR $v_{max}$ (cm$^{-1}$) 3358, 2971, 2867, 1631; HRMS (ESI) calcd for C$_{12}$H$_{18}$N$_2$O (M+) 207.1492. found 207.1489.

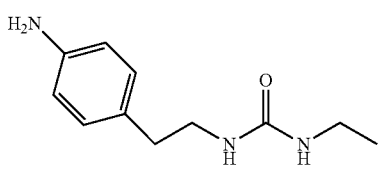

1-(4-aminophenethyl)-3-ethylurea (8g): Light yellow solid. mp=101-103° C. ¹H NMR (300 MHz, CDCl₃) δ 6.94 (d, J=8.4, 2 H), δ 6.58 (d, J=6.0 Hz, 2H), δ 5.05 (t, J=3.3 Hz, 2H), δ 3.59 (s, 2H), δ 3.28 (q, J=6.9, 6.9 Hz, 2H), δ 3.10 (m, 2H), δ 2.63 (t, J=6.9 Hz, 2H), δ 1.04 (t, J=7.2, 3 H) ppm; ¹³C NMR (75 MHz, CDCl₃) δ 159.0, 145.0, 129.8, 115.5, 42.1, 35.9, 15.7 ppm; IR $\nu_{max}$ (cm⁻¹) 3409, 1635, 1517, 1263; HRMS (ESI) calcd for $C_{11}H_{17}N_3O$ (M+) 208.1444. found 208.1445.

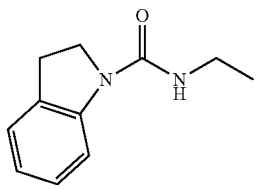

N-ethylindoline-1-carboxamide (6 g): Light yellow solid. mp=111-113° C. ¹H NMR (300 MHz, CDCl₃) δ 7.90 (d, J=8.1 Hz, 1H), δ 7.11-7.04 (m, 2H), δ 6.82 (t, J=7.5 Hz, 1H), δ 5.09 (s, 1H), δ 3.78 (t, J=8.7 Hz, 2H), δ 3.27 (m, 2H), δ 3.02 (t, J=9.0 Hz, 2H), δ 1.15 (t, J=7.2 Hz, 3H) ppm; ¹³C NMR (75 MHz, CDCl₃) δ ppm; IR $\nu_{max}$ (cm⁻¹) 3403, 2959, 1646; HRMS (ESI) calcd for $C_{11}H_{14}N_2O$ (M+) 190.1179. found 190.1177.

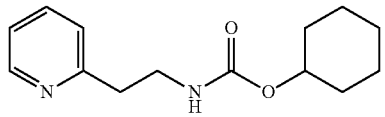 [SMILES: O=C(NCCc1ccccn1)OC1CCCCC1]

cyclohexyl 2-(pyridin-2-yl)ethylcarbamate (9l): Colorless oil. ¹H NMR (300 MHz, CDCl₃) δ 8.33 (d, J=4.8 Hz, 1H), δ 7.43 (t, J=9.9 Hz, 1H), δ 7.02-6.94 (m, 2H), δ 5.72 (s, 1H), δ 4.45 (d, J=3.6 Hz, 1H), δ 3.40 (q, J=6.6, 6.3 Hz, 2H), δ 2.83 (t, J=6.6 Hz, 2H), δ 1.702-1.027 (m, 10H) ppm; ¹³C NMR (75 MHz, CDCl₃) δ 159.4, 156.5, 149.1, 136.8, 123.6, 121.6, 40.4, 37.9, 32.2, 25.5, 23.9 ppm; IR $\nu_{max}$ (cm⁻¹) 3944, 3692, 3054, 2987, 1709; HRMS (ESI) calcd for $C_{14}H_{20}N_2O_2$ (M+) 249.1598. found 249.1595.

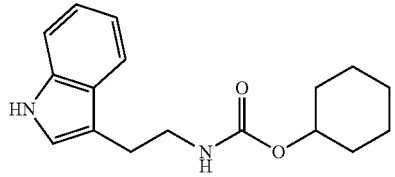 [SMILES: O=C(NCCc1c[nH]c2ccccc12)OC1CCCCC1]

cyclohexyl 2-(1H-indol-3-yl)ethylcarbamate (10l): Colorless oil. ¹H NMR (300 MHz, CDCl₃) δ 8.74 (s, 1H), δ 7.65 (d, J=6.9 Hz, 1H), δ 7.38 (d, J=7.2 Hz, 1H), δ 7.20 (dd, J=7.2, 7.2 Hz, 2H), δ 6.96 (s, 1H), δ 4.94 (s, 1H), δ 4.72 (s, 1H), δ 3.63 (d, J=34.2 Hz, 2H), δ 2.98 (s, 2H), δ 1.91-1.31 (m, 10H) ppm; ¹³C NMR (75 MHz, CDCl₃) δ 156.8, 136.8, 127.6, 122.6, 119.5, 112.8, 73.3, 70.6, 41.6, 35.8, 32.4, 26.1, 24.5 ppm; IR $\nu_{max}$ (cm⁻¹) 3334, 2909, 2991, 1701; HRMS (ESI) calcd for $C_{17}H_{22}N_2O_2$(M+) 287.1755. found 287.1752.

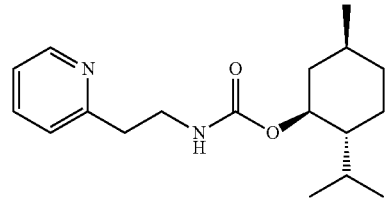 [SMILES: CC(C)[C@H]1CC[C@H](C)C[C@@H]1OC(=O)NCCc1ccccn1]

(1S,2R,5S)-2-isopropyl-5-methylcyclohexyl 2-(pyridin-2-yl)ethylcarbamate (9k): Yellow solid. mp=57-59° C. ¹H NMR (300 MHz, CDCl₃) δ 8.37 (d, J=4.5 Hz, 1H), δ 7.45 (t, J=5.7 Hz, 1H), δ 6.98 (m, 2H), δ 5.55 (s, 1H), δ 4.40 (t, J=3.9 Hz, 1H), δ 3.43 (q, J=6.3 Hz, 2H), δ 2.85 (t, J=6.3 Hz, 2H), δ 2.01-0.62 (m, 19H) ppm; ¹³C NMR (75 MHz, CDCl₃) δ 159.5, 156.7, 136.3, 123.6, 121.6, 74.2, 47.5, 41.6, 40.4, 37.9, 34.4, 31.5, 26.7, 23.6, 22.2, 20.9, 16.6 ppm; IR $\nu_{max}$ (cm⁻¹) 3406, 2954, 2868, 1695, 1694, 1514, 1260; HRMS (ESI) calcd for $C_{18}H_{28}N_2O_2$(M+) 305.2224. found 305.2221.

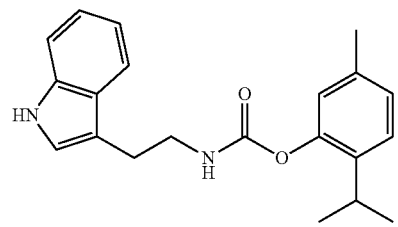 [SMILES: Cc1ccc(C(C)C)c(OC(=O)NCCc2c[nH]c3ccccc23)c1]

2-isopropyl-5-methylphenyl 2-(1H-indol-3-yl)ethylcarbamate (10i): Colorless oil. ¹H NMR (300 MHz, CDCl₃) δ 8.71 (s, 1H), δ 7.67 (d, J=7.5, 1 H), δ 7.37 (d, J=8.1 Hz, 1H), δ 7.25 (t, J=7.2 Hz, 1H), δ 7.20 (t, J=7.2 Hz, 1H), δ 6.96 (s, 1H), δ 4.92 (s, 1H), δ 3.52 (t, J=6.3 Hz, 2H), δ 3.01 (t, J=6.3 Hz, 2H), δ 1.26-1.03 (m, 6H), δ 0.99 (d, J=6.6 Hz, 3H), δ 0.95 (d, J=6.9 Hz, 3H) ppm; ¹³C NMR (75 MHz, CDCl₃) δ 157.1, 136.8, 127.7, 122.6, 119.0, 112.9, 111.7, 74.9, 47.6, 41.8, 34.6, 31.7, 26.5, 23.8, 22.4, 21.2, 16.8 ppm; IR $\nu_{max}$ (cm⁻¹) 3408, 2962, 2926, 1717, 1620, 1502, 1457; HRMS (ESI) calcd for $C_{21}H_{24}N_2O_2$(M+) 337.1911. found 337.1914.

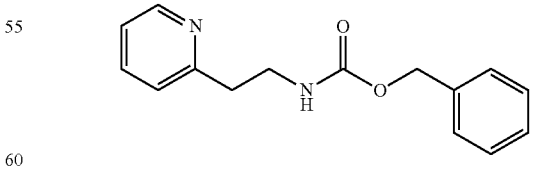

benzyl 2-(pyridin-2-yl)ethylcarbamate (9c): Colorless oil. ¹H NMR (300 MHz, CDCl₃) δ 8.34 (d, J=6.6 Hz, 1H), δ 7.46 (t, J=7.8 Hz, 1H), δ 6.98 (dd, J=7.8, 7.5 Hz, 2H), δ 5.72 (s, 1H), δ 4.45 (d, J=7.2 Hz, 1H), δ 3.42 (q, J=6.6, 6.3 Hz, 2H), δ 2.83 (t, J=6.6 Hz, 2H), δ 1.70-1.03 (m, 10H) ppm; ¹³C NMR (75 MHz, CDCl₃) δ 159.4, 156.5, 149.1, 136.8, 123.6, 121.6, 72.8, 40.4, 37.86, 32.2, 25.5, 23.9 ppm; IR $\nu_{max}$ (cm$^{-1}$) 3435, 2092, 1644, 1261; HRMS (ESI) calcd for $C_{15}H_{16}N_2O_2$ (M+) 257.1285. found 257.1282.

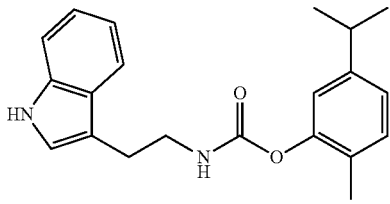 [SMILES: Cc1ccc(C(C)C)cc1OC(=O)NCCc1c[nH]c2ccccc12]

5-isopropyl-2-methylphenyl 2-(1H-indol-3-yl)ethylcarbamate (10j): $^1$H NMR (300 MHz, CDCl$_3$) δ 8.47 (s, 1H), δ 7.74 (d, J=7.8 Hz, 1H), δ 7.37-7.05 (m, 6H), δ 6.95 (s, 1H), 5.35 (s, 1H), δ 3.69 (t, J=6.6 Hz, 2H), δ 3.10 (t, J=6.6 Hz, 2H), δ 2.96 (m, 1H), δ 2.24 (s, 3H), δ 1.33 (d, J=6.6 Hz, 6H) ppm; $^{13}$C NMR (75 MHz, CDCl$_3$) δ 155.24, 149.7, 148.4, 136.8, 131.2, 128.2, 124.7, 122.7, 120.6, 119.6, 118.9, 112.5, 42.0, 33.9, 26.0, 24.3, 16.1 ppm; IR $\nu_{max}$ (cm$^{-1}$) 3336, 2969, 2926, 1719, 1503, 1457; HRMS (ESI) calcd for $C_{21}H_{24}N_2O_2$ (M+) 337.1911. found 337.1914.

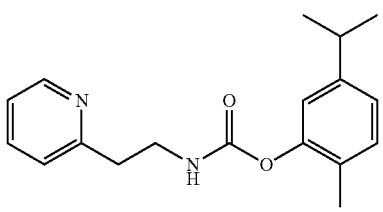 [SMILES: Cc1ccc(C(C)C)cc1OC(=O)NCCc1ccccn1]

5-isopropyl-2-methylphenyl 2-(pyridin-2-yl)ethylcarbamate (9j): $^1$H NMR (300 MHz, CDCl$_3$) δ 8.55 (d, J=3.9 Hz, 1H), δ 7.67 (t, J=7.8 Hz, 1H), δ 7.27-6.88 (m, 5H), δ 6.46 (t, J=5.4 Hz, 1H), δ 3.68 (q, J=6.6, 6.3 Hz, 2H), δ 3.12 (t, J=6.6 Hz, 2H), δ 2.83 (m, 1H), δ 2.13 (s, 3H), δ 1.23 (d, J=5.1 Hz, 6H) ppm; $^{13}$C NMR (75 MHz, CDCl$_3$) δ 158.7, 155.0, 149.6, 148.1, 138.4; 131.0, 128.0, 124.5, 123.9, 122.4, 120.4, 40.8, 37.0, 33.8, 24.2, 15.9 ppm; IR $\nu_{max}$ (cm$^{-1}$) 3054, 2987, 2306, 1734, 1501; HRMS (ESI) calcd for $C_{18}H_{22}N_2O_2$ (M+) 299.1755. found 299.1753.

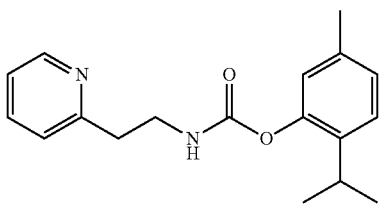 [SMILES: Cc1ccc(C(C)C)c(OC(=O)NCCc2ccccn2)c1]

2-isopropyl-5-methylphenyl 2-(pyridin-2-yl)ethylcarbamate (9i): $^1$H NMR (300 MHz, CDCl$_3$) δ 8.54 (d, J=4.8 Hz, 1H), δ 7.65 (t, J=7.5 Hz, 1H), δ 7.25-6.94 (m, 4H), δ 6.83 (s, 1H), δ 6.47 (s, 1H), δ 3.68 (q, J=6.0, 6.0 Hz, 2H), δ 3.07 (m, 2H), δ 2.27 (s, 3H), δ 1.16 (d, J=6.0 Hz, 6H) ppm; $^{13}$C NMR (75 MHz, CDCl$_3$) δ 158.8, 155.4, 148.4, 138.2, 137.8, 136.5, 126.9, 126.5, 124.4, 123.4, 122.3, 40.8, 37.1, 27.1, 23.3, 21.1 ppm; IR $\nu_{max}$ (cm$^{-1}$) 3054, 2966, 1735, 1250; HRMS (ESI) calcd for $C_{18}H_{22}N_2O_2$(M+) 299.1755. found 299.1759.

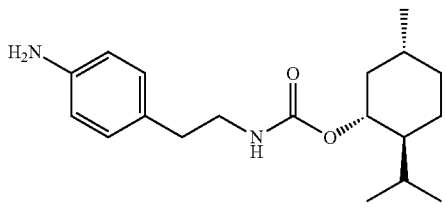 [SMILES: CC(C)[C@@H]1CC[C@@H](C)C[C@H]1OC(=O)NCCc1ccc(N)cc1]

(1R, 2S, 5R)-2-isopropyl-5-methylcyclohexyl 4-aminophenethylcarbamate (8a): $^1$H NMR (300 MHz, CDCl$_3$) δ 6.93 (d, J=8.1 Hz, 2H), δ 6.60 (d, J=8.4 Hz, 2H), δ 4.79 (t, J=5.7 Hz, 1H), δ 4.53 (t, J=3.9 Hz, 1H), δ 3.59 (s, 2H), δ 3.33 (q, J=4.5, 5.7 Hz, 2H), δ 2.65 (t, J 6.6 Hz, 2H), δ 2.03 (d, J=6.9 Hz, 1H), δ 1.87 (t, 6.6 Hz, 1H), δ 1.65 (d, 10.5 Hz, 2H), S 1.43 (s, 3H), δ 1.25 (t, 6.4 Hz, 1H), δ 1.01 (q, J=2.7, 2.7 Hz, 1H), δ 0.92 (m. 6H), δ 0.79 (d, J=7.2 Hz, 3H) ppm; $^{13}$C NMR (75 MHz, CDCl$_3$) δ 156.7, 145.1, 129.8, 128.9, 115.6, 47.6, 42.6, 41.7, 35.4, 34.5, 31.6, 26.5, 23.8, 22.3, 21.1, 16.7 ppm; IR $\nu_{max}$ (cm$^{-1}$) 3442, 2955, 2869, 1698, 1626, 1264; HRMS (ESI) calcd for $C_{19}H_{30}N_2O_2$(M+) 319.2381. found 319.2383.

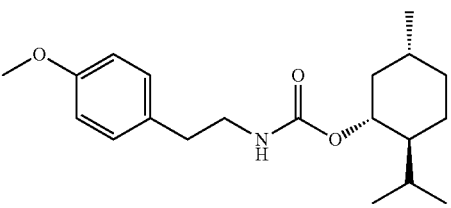 [SMILES: COc1ccc(CCNC(=O)O[C@@H]2C[C@H](C)CC[C@H]2C(C)C)cc1]

(1R, 2S, 5R)-2-isopropyl-5-methylcyclohexyl 4-methoxyphenethylcarbamate (12a): White solid. mp=95-98° C. $^1$H NMR (300 MHz, CDCl$_3$) δ 7.09 (d, J=8.7 Hz, 2H), δ 6.84 (d, J=8.7 Hz, 2H), δ 4.78 (t, J=5.7 Hz, 1H), 4.56 (t, 3.9 Hz, 1H), δ 3.74 (s, 3H), δ 3.36 (q, J=6.6, 5.7 Hz, 2H), δ 2.73 (t, 7.2 Hz, 2H), δ 1.99 (d, J=4.8 Hz, 1H), δ 1.66 (t, J=10.2 Hz, 1H), δ 1.48 (d, J=3.0 Hz, 2H), δ 1.47 (t, J=3.3 Hz, 1H), δ 1.07 (t, 3.5 Hz, 1H), δ 1.03 (q, 3.5, 3.0 Hz, 1H), δ 0.93 (m, 6H), δ 0.80 (d, 7.2 Hz, 3H) ppm; $^{13}$C NMR (75 MHz, CDCl$_3$) δ 158.4, 156.7, 131.1, 129.9, 114.2, 55.4, 47.6, 41.7, 35.5, 34.6, 31.6, 26.5, 23.8, 22.3, 21.1, 16.7 ppm; IR $\nu_{max}$ (cm$^{-1}$) 3372, 2954, 2869, 1684, 1512, 1455, 1242, 1178, 1127, 1056, 623; HRMS (ESI) calcd for $C_{20}H_{31}NO_3$ (M+) 356.2196. found 356.2199.

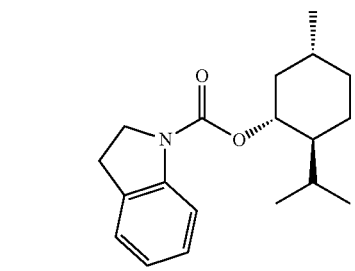 [SMILES: CC(C)[C@@H]1CC[C@@H](C)C[C@H]1OC(=O)N1CCc2ccccc21]

(1R, 2S, 5R)-2-isopropyl-5-methylcyclohexyl indoline-1-carboxylate (6a): Colorless oil. $^1$H NMR (300 MHz, CDCl$_3$) δ 7.90 (s, 1H), δ 7.26 (m, 2H), δ 6.91 (m, 1H), δ 4.75 (s, 1H), δ 3.99 (s, 2H), δ 3.89 (t, 6 Hz, 2H), δ 2.19 (d, J=8.7 Hz, 1H), δ 1.95 (s, 1H), δ 1.55 (d, J=2.4 Hz, 2H), δ 1.41 (s, 2H), δ 1.12 (m, 2H), δ 0.84 (m, 10H) ppm; $^{13}$C NMR (75 MHz, CDCl$_3$) δ 127.7, 124.9, 122.5, 114.9, 47.8, 41.9, 34.7, 34.6, 31.7, 27.6, 26.7, 26.6, 23.8, 22.3, 21.1, 16.8, 16.7 ppm; IR ν$_{max}$ (cm$^{-1}$) 3428, 2955, 2869, 1704, 1604, 1488; HRMS (ESI) calcd for C$_{19}$H$_{27}$NO$_2$ (M+) 324.1934. found 324.1929.

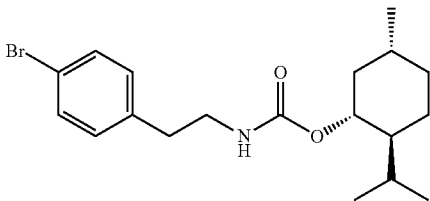 [SMILES: CC(C)[C@@H]1CC[C@@H](C)C[C@H]1OC(=O)NCCc1ccc(Br)cc1]

(1R, 2 S, 5R)-2-isopropyl-5-methylcyclohexyl 4-bromophenethylcarbamate (11a): White solid. mp=104-106° C. $^1$H NMR (300 MHz, CDCl$_3$) δ 7.38 (d, J=5.7 Hz, 2H), δ 7.03 (d, 6 Hz, 2H), δ 4.74 (s, 1H), δ 4.51 (t, J=2.7 Hz, 1H), δ 3.35 (d, J=4.5 Hz, 2H), δ 2.73 (s, 2H), δ 1.99 (d, J=9.0 Hz, 1H), δ 1.64 (t, J=1.5 Hz, 1H), δ 1.63 (t, J=2.4 Hz, 2H), δ 1.41 (m, 1H), 1.04 (t, J=3.8 Hz, 1H), δ 1.03 (q, J=2.4 Hz, 2H) δ 0.97 (m, 6H), δ 0.76 (d, J=5.1 Hz, 3H) ppm; $^{13}$C NMR (75 MHz, CDCl$_3$) δ 1.56.6, 138.1, 131.8, 130.8, 120.5, 74.7, 47.6, 42.1, 41.7, 35.8, 34.5, 31.6, 26.5, 23.8, 22.3, 21.0, 16.7 ppm; IR ν$_{max}$ (cm$^{-1}$) 3364, 2953, 2856, 1684, 1256; HRMS (ESI) calcd for C$_{19}$H$_{28}$BrNO$_2$(M+) 404.1196. found 404.1191.

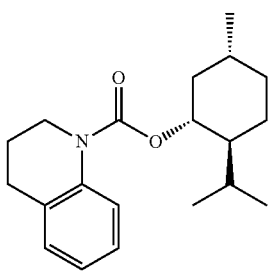 [SMILES: CC(C)[C@@H]1CC[C@@H](C)C[C@H]1OC(=O)N1CCCc2ccccc21]

(1R, 2 S, 5R)-2-isopropyl-5-methylcyclohexyl 3,4-dihydroquinoline-1(2H)-carboxylate (7a): Colorless oil. $^1$H NMR (300 MHz, CDCl$_3$) δ 7.76 (d, J=8.4 Hz, 1H), δ 7.18 (t, J=1.5 Hz, 1H), δ 7.13 (d, J=1.8 Hz, 1H), δ 6.97, J=0.9 Hz, 1H), δ 4.77 (t, J=4.2 Hz, 1H), δ 3.77 (t, J=0.9 Hz, 2H), δ 2.78 (t, J=6.6 Hz, 2H), δ 1.18 (d, J=3.0 Hz, 1H), δ 1.99 (m, 3H), δ 1.68 (d, J=2.7 Hz, 2H), δ 1.414 (m, 2H), δ 1.13 (m, 2H), δ 1.10 (m, 6H), δ 0.87 (d, J=7.2 Hz, 3H) ppm; $^{13}$C NMR (75 MHz, CDCl$_3$) δ 154.9, 138.7, 129.9, 128.8, 126.1, 124.2, 123.6, 76.5, 47.5, 44.9, 41.7, 34.6, 31.7, 27.7, 26.7, 23.8, 23.8, 22.3, 21.1, 16.7 ppm; IR ν$_{max}$ (cm$^{-1}$) 3434, 2954, 2870, 2105, 1694; HRMS (ESI) calcd for C$_{20}$H$_{29}$NO$_2$ (M+) 338.2091. found 338.2088.

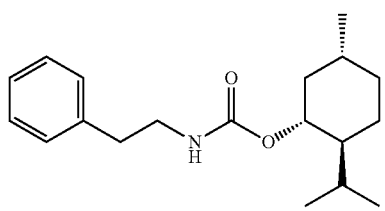 [SMILES: CC(C)[C@@H]1CC[C@@H](C)C[C@H]1OC(=O)NCCc1ccccc1]

(1R, 2 S, 5R)-2-isopropyl-5-methylcyclohexyl phenethylcarbamate (2a): White solid. mp=84-86° C. $^1$H NMR (300 MHz, CDCl$_3$) δ 7.29 (m, 5H), δ 4.91 (t, J=4.2 Hz, 1H), δ 4.58 (s, 1H), δ 3.39 (s, 2H), δ 2.79 (t, J=7.8 Hz, 2H), δ 2.05 (d, J=8.7 Hz, 1H), δ 1.93 (t, J=4.2 Hz, 1H), δ 1.66 (s, 2H), δ 1.47 (s, 1H), δ 1.28 (t, J=3.8 Hz, 1H), δ 1.04 (q, 10.2, 9.3 Hz, 2H), δ 0.91 (m, 8H), δ 0.80 (d, J=0.60, 3 H) ppm; $^{13}$C NMR (75 MHz, CDCl$_3$) δ 156.7, 139.2, 129.1, 128.9, 128.8, 128.7, 126.6, 126.5, 74.6, 47.6, 45.3, 42.4, 41.9, 41.8, 36.5, 34.9, 31.6, 26.5, 23.8, 23.4, 22.6, 22.3, 21.1, 16.4 ppm; IR ν$_{max}$ (cm$^{-1}$) 3360, 2957, 1682, 1526, 1259, 1024, 798; HRMS (ESI) calcd for C$_{19}$H$_{29}$NO$_2$ (M+) 343.2381. found 343.2383.

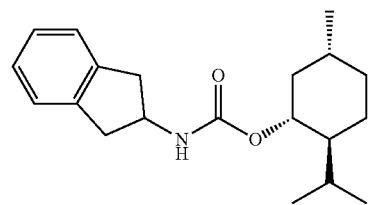 [SMILES: CC(C)[C@@H]1CC[C@@H](C)C[C@H]1OC(=O)NC1Cc2ccccc2C1]

(1R, 2 S, 5R)-2-isopropyl-5-methylcyclohexyl 2,3-dihydro-1H-inden-2-ylcarbamate (3a): White solid. mp=167-170° C. $^1$H NMR (300 MHz, CDCl$_3$) δ 7.19 (m, 4H), δ 4.99 (s, 1H), δ 4.57 (m, 2H), δ 3.25 (m, 3H), δ 2.75 (m, 2H), δ 2.02 (d, J=11.7 Hz, 2H), δ 1.94 (t, J=2.1 Hz, 1H), δ 1.67 (d, J=12.9, 2 H), δ 1.58 (s, 1H), δ 1.45 (t, J=3.3 Hz, 1H), 1.05 (q, J=3.0, 7.5 Hz, 2H), δ 0.93 (m, 6H), δ 0.78 (d, J=7.2 Hz, 6H) ppm; $^{13}$C NMR (75 MHz, CDCl$_3$) δ 159.6, 126.9, 126.8, 124.9, 124.8, 51.6, 50.3, 47.6, 45.3, 41.7, 40.8, 40.6, 34.8, 34.5, 31.0, 31.6, 26.5, 23.7, 23.4, 22.5, 22.3, 21.3, 21.1, 16.6, 16.3 ppm; IR ν$_{max}$ (cm$^{-1}$) 3409, 1688; HRMS (ESI) calcd for C$_{20}$H$_{29}$NO$_2$ (M+) 338.2091. found 338.2098.

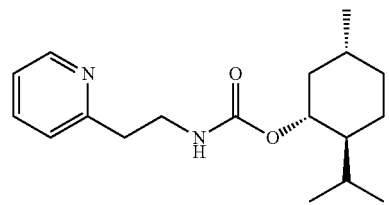 [SMILES: CC(C)[C@@H]1CC[C@@H](C)C[C@H]1OC(=O)NCCc1ccccn1]

(1R, 2 S, 5R)-2-isopropyl-5-methylcyclohexyl 2-(pyridin-2-yl)ethylcarbamate (9a): White solid. mp=59-63° C. $^1$H NMR (300 MHz, CDCl$_3$) δ 8.50 (q, J=0.6, 2.4 Hz, 1H), δ 7.61 (t, J=2.1 Hz, 1H), δ 7.13 (m, 2H), δ 5.75 (s, 1H), δ 4.54 (t, J=7.2 Hz, 1H), δ 3.59 (q, J=5.7, 6.3 Hz, 2H), δ 2.99 (t, J=6.3 Hz, 2H), δ 2.03 (d, J=11.7 Hz, 1H), δ 1.89 (m, 1H), δ 1.59 (tm, 2H), δ 1.27 (s, 1H), δ 1.27 (t, J=10.8 Hz, 1H), δ 0.97 (m, 2H), δ 0.91 (m, 6H), δ 0.76 (d, J=6.9 Hz, 3H) ppm; $^{13}$C NMR (75 MHz, CDCl$_3$) δ 159.5, 156.6, 140.3, 136.5, 123.6, 121.5, 74.2, 71.1, 50.1, 47.5, 41.6, 40.4, 37.9, 34.7, 31.8, 31.4, 26.3, 23.6, 20.9, 16.2 ppm; IR ν$_{max}$ (cm$^{-1}$) 3406, 2954, 2868, 1695, 1694, 1514, 1260; HRMS (ESI) calcd for C$_{18}$H$_{28}$N$_2$O$_2$(M+) 305.2224. found 305.2229.

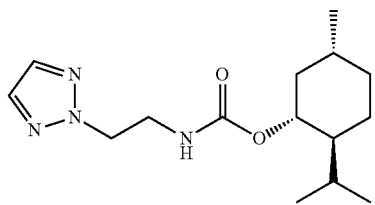 [SMILES: CC(C)[C@@H]1CC[C@@H](C)C[C@H]1OC(=O)NCCn1nccn1]

(1R, 2 S, 5R)-2-isopropyl-5-methylcyclohexyl 2-(2H-1,2,3-triazol-2-yl)ethylcarbamate (5a): White residue. $^1$H NMR (300 MHz, CDCl$_3$) δ 7.59 (s, 2H), δ 5.11 (s, 1H), δ 4.54 (s, 2H), δ 3.72 (s, 2H), δ 3.24 (s, 1H), δ 1.90 (m, 2H), δ 1.61 (s, 1H), δ 1.52 (s, 2H), δ 1.45 (s, 1H), δ 1.24 (s, 1H), 1.09 (m, 2H), δ 1.05 (m, 8H), S 0.76 (d, J=4.2 Hz, 3H) ppm; $^{13}$C NMR (75 MHz, CDCl$_3$) S 156.5, 134.6, 74.8, 71.7, 54.7, 50.3, 47.7, 47.5, 41.8, 40.5, 34.5, 31.6, 26.5, 23.7, 22.2, 16.3 ppm; IR ν$_{max}$ (cm$^{-1}$) 3434, 2955, 2088, 1642, 1256; HRMS (ESI) calcd for C$_{15}$H$_{26}$N$_4$O$_2$ (M+) 304.4125. found 304.4129.

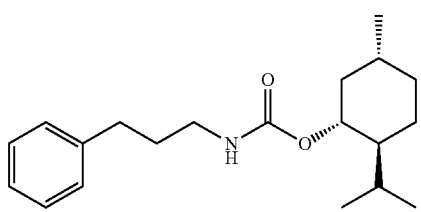 [SMILES: CC(C)[C@@H]1CC[C@@H](C)C[C@H]1OC(=O)NCCCc1ccccc1]

(1R, 2 S, 5R)-2-isopropyl-5-methylcyclohexyl 3-phenylpropylcarbamate (4a): White solid. mp=75-78° C. $^1$H NMR (300 MHz, CDCl$_3$) δ 7.28 (t, J=7.8 Hz, 2H), δ 7.16 (d, J=7.2 Hz, 2H), δ 4.86 (s, 1H), δ 4.55 (t, J=6.9 Hz, 1H), δ 3.201 (q, J=6.6, 6.0 Hz, 2H), S 2.64 (t, J=7.5 Hz, 2H), S 2.05 (d, J=11.7 Hz, 1H), δ 1.95 (t, J=2.7 Hz, 1H), δ 1.89 (m, 2H), S 1.66 (d, J=10.8 Hz, 2H), S 1.48 (s, 1H), δ 1.06 (t, J=8.4 Hz, 1H), δ 1.06 (m, 2H), δ 1.02 (m, 8H), δ 0.80 (d, J=6.9 Hz, 3H) ppm; $^{13}$C NMR (75 MHz, CDCl$_3$) δ 156.9, 141.8, 128.7, 128.6, 126.2, 126.1, 74.6, 47.4, 41.8, 40.1, 34.6, 33.5, 33.3, 31.9, 31.6, 26.6, 23.8, 22.4, 16.8 ppm; IR ν$_{max}$ (cm$^{-1}$) 3410, 3057, 2960, 1713, 1421, 1362, 1267, 1222, 191, 846, 736, 702; HRMS (ESI) calcd for C$_{20}$H$_{31}$NO$_2$ (M+) 340.2247. found 340.2241.

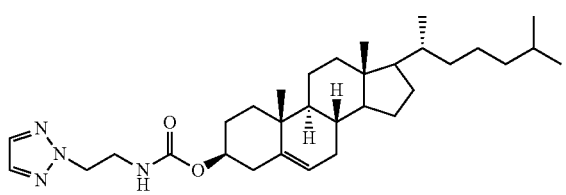

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2-(2H-1,2,3-triazol-2-yl)ethylcarbamate (5f): White solid. mp=135-139° C. $^1$H NMR (300 MHz, CDCl$_3$) δ 7.58 (s, 2H), δ 5.31 (t, 6.9 Hz, 1H), δ 4.53 (t, J=5.1 Hz, 1H), δ 3.69 (q, J=5.1 Hz, 2H) δ 3.47 (m, 2H), δ 2.49 (s, 1H), δ 2.45 (q, J=9.3, 4.2 Hz, 2H), δ 1.96 (m, 6H), δ 1.54-1.30 (m, 11H), δ 1.25-1.09 (m, 14H), δ1.01-0.82 (m, 10H), 80.65 (s, 3H) ppm; $^{13}$C NMR (75 MHz, CDCl$_3$) δ141.1, 134.6, 121.8, 71.8, 57.0, 56.9, 50.3, 42.5, 40.0, 39.8, 37.5, 36.7, 36.4, 36.1, 32.1, 31.8, 28.5, 28.2, 24.5, 24.1, 23.1, 229, 21.3, 19.6, 19.5, 18.9, 12.1 ppm; IR ν$_{max}$ (cm$^{-1}$) 3398, 2037, 1637; HRMS (ESI) calcd for C$_{32}$H$_{52}$N$_4$O$_2$ (M+) 547.3982. found 547.3981.

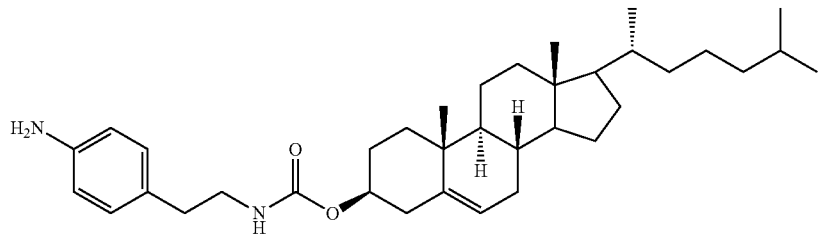

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-aminophenethylcarbamate (80: Yellow hygroscopic solid. $^1$H NMR (300 MHz, CDCl$_3$) δ 6.93 (d, J=7.5 Hz, 2H), δ 6.588 (d, J=7.5 Hz, 2H), δ 5.35 (m, 1H), δ 4.92 (s, 1H), δ 4.47 (m, 1H), δ 3.32 (d, J=6.0 Hz, 2H), δ 2.54 (t, J=6.6 Hz, 2H), δ 2.31 (m, 2H), δ 2.02-1.98 (m, 5H), δ 1.54-1.27 (m, 11H), δ 1.10-0.85 (m, 24H), δ 0.67 (s, 3H) ppm; $^{13}$C NMR (75 MHz, CDCl$_3$) δ 156.4, 145.2, 141.2, 140.1, 129.8, 128.8, 122.7, 115.6, 74.4, 57.-, 56.9, 56.4, 50.2, 42.6, 40.0, 39.8, 38.9, 37.3, 36.8, 36.5, 35.5, 32.1, 31.8, 28.4, 28.3, 24.5, 24.2, 23.2, 22.0, 21.3, 10.7, 19.5, 19.0, 12.1 ppm; IR ν$_{max}$ (cm$^{-1}$) 3407, 2937, 2868, 2245, 1695, 1631, 1516; HRMS (ESI) calcd for C$_{36}$H$_{56}$N$_2$O$_2$ (M+) 549.4415. found 549.4420.

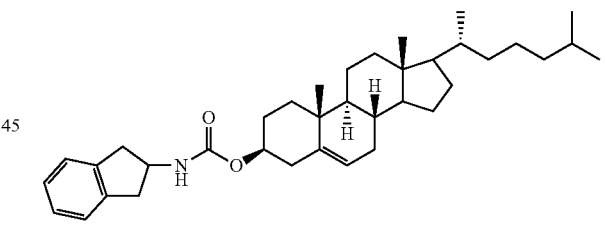

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2,3-dihydro-1H-inden-2-ylcarbamate (3f): mp=114-116° C. $^1$H NMR (300 MHz, CDCl$_3$) δ 7.19 (m, 4H), δ 5.37 (d, J=6.6 Hz, 1H), δ 5.15 (m, 1H), S 4.52 (s, 1H), δ 3.40 (m, 1H), δ 3.24 (m, 2H), δ 2.78 (m, 2H), δ 2.27 (m, 3H), δ 2.04-1.84 (m, 5H), δ 1.55-1.26 (m, 11H), δ 1.12-0.87 (m, 23H), δ 0.69 (s, 3H) ppm; $^{13}$C NMR (75 MHz, CDCl$_3$) δ 141.4, 126.9, 125.0, 124.9, 122.8, 121.89, 71.9, 57.0, 56.9, 56.4, 52.4, 51.7, 50.4, 50.2, 42.5, 42.5, 40.8, 40.5, 40.1, 40.0, 39.8, 37.6, 36.8, 36.5, 36.1, 32.2, 32.1, 31.8, 28.5, 28.5, 24.6, 24.2, 23.1, 22.9, 21.4, 21.3, 19.7, 19.6, 19.0, 12.1 ppm; IR ν$_{max}$ (cm$^{-1}$) 3358, 2937, 2867, 1693, 1551, 1466; HRMS (ESI) calcd for C$_{37}$H$_{55}$NO$_2$ (M+) 568.4125. found 568.4136.

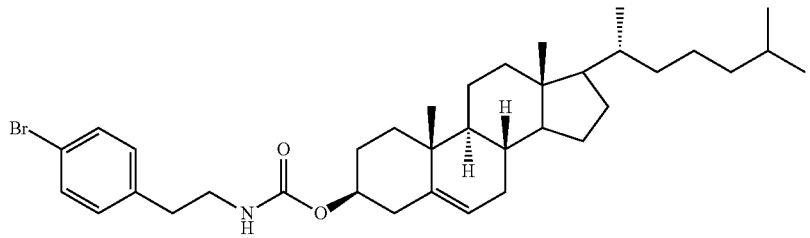

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-bromophenethylcarbamate (110: White solid. mp=142-145° C. $^1$H NMR (300 MHz, CDCl$_3$) δ 7.37 (d, J=8.4 Hz, 2H), δ 6.99 (d, J=8.4 Hz, 2H), δ 5.34 (s, 1H), δ 4.98 (t, J=5.7, 1 H), δ 4.44 (m, 1H), δ 3.34 (q, J=6.6 Hz, 1H), δ 2.72 (t, J=6.6 Hz, 2H), δ 2.27 (m, 2H), δ 2.32-1.79 (m, 5H), δ 1.52-1.34 (m, 11H), δ 1.22-0.86 (m, 22H), δ 0.65 (s, 3H) ppm; $^{13}$C NMR (75 MHz, CDCl$_3$) δ 202.3, 156.3, 139.1, 138.1, 131.9, 131.7, 130.8, 122.8, 120.5, 74.5, 56.9, 57.4, 50.2, 42.5, 42.1, 39.9, 39.8, 38.8, 37.3, 36.8, 36.5, 36.1, 32.1, 29.6, 28.4, 28.2, 24.5, 24.2, 23.1, 22.9, 21.3, 19.6, 19.0, 12.1 ppm; IR ν$_{max}$ (cm$^{-1}$) 3435, 2947, 2867, 2249, 1793, 1488; HRMS (ESI) calcd for C$_{36}$H$_{54}$BrNO$_2$ (M+) 634.3230. found 634.3210.

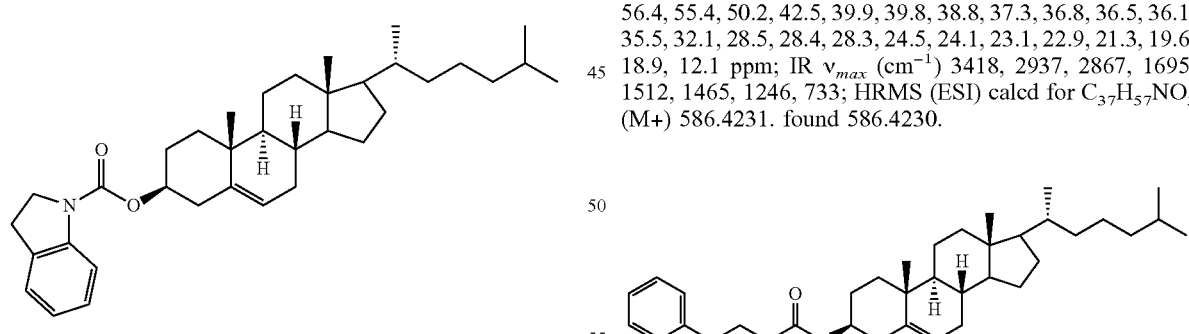

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl indoline-1-carboxylate (6f): White solid. mp=157-159° C. $^1$H NMR (300 MHz, CDCl$_3$) δ 7.86 (s, 1H), δ 7.16 (t, 2H), δ 6.93 (t, J=7.5 Hz, 1H), δ 5.44 (d, J=4.5 Hz, 1H), δ 4.68 (s, 1H), δ 3.98 (t, J=7.5 Hz, 2H), δ 3.07 (t, J=8.7 Hz, 2H), δ 2.07-1.84 (m, 5H), δ 1.59-1.28 (m, 11H), δ 1.21-1.04 (m, 10H), δ 1.03-0.90 (m, 12H), δ 0.72 (s, 3H) ppm; $^{13}$C NMR (75 MHz, CDCl$_3$) δ 202.3, 149.9, 139.9, 127.7, 122.9, 122.6, 115.1, 75.1, 56.9, 56.5, 50.3, 47.6, 42.6, 40.0, 39.8, 37.7, 37.3, 36.8, 36.8, 36.4, 32.2, 32.1, 31.8, 28.6, 28.3, 27.6, 24.6, 24.3, 23.2, 22.9, 21.4, 19.7, 19.0, 12.2 ppm; IR ν$_{max}$ (cm$^{-1}$) 3444, 2944, 1699, 1604; HRMS (ESI) calcd for C$_{36}$H$_{53}$NO$_2$ (M+) 532.4150. found 532.4152.

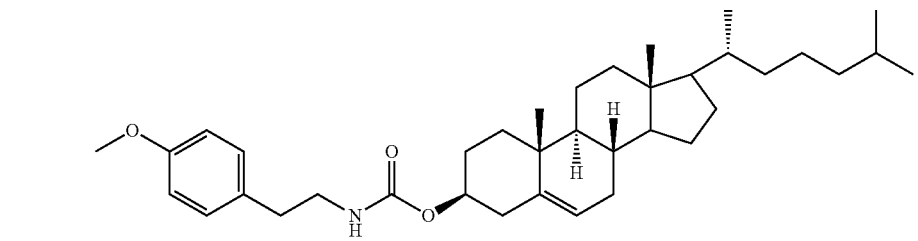

(3 S, 8 S, 9S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-methoxyphenethylcarbamate (12f): White residue. $^1$H NMR (300 MHz, CDCl$_3$) δ 7.10 (d, J=6.6 Hz, 2H), δ 6.83 (d, J=6.6 Hz, 2H), δ 5.37 (d, J=4.8 Hz, 1H), δ 4.88 (s, 1H), δ 4.48 (m, 1H), δ 3.75 (s, 3H), δ 3.36 (q, J=6.0, 6.6 Hz, 2H), δ 2.72 (t, J=6.9 Hz, 2H), δ 2.32 (m, 2H), δ 1.98-1.81 (m, 5H), δ 1.52-1.36 (m, 11H), δ 1.28-1.13 (m, 12H), δ 1.11-0.86 (m, 10H), δ 0.67 (s, 3H) ppm; $^{13}$C NMR (75 MHz, CDCl$_3$) δ 158.5, 156.4, 140.0, 131.1, 129.9, 122.7, 114.2, 114.1, 74.5, 56.9, 56.4, 55.4, 50.2, 42.5, 39.9, 39.8, 38.8, 37.3, 36.8, 36.5, 36.1, 35.5, 32.1, 28.5, 28.4, 28.3, 24.5, 24.1, 23.1, 22.9, 21.3, 19.6, 18.9, 12.1 ppm; IR ν$_{max}$ (cm$^{-1}$) 3418, 2937, 2867, 1695, 1512, 1465, 1246, 733; HRMS (ESI) calcd for C$_{37}$H$_{57}$NO$_3$ (M+) 586.4231. found 586.4230.

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl phenethylcarbamate (2f): White solid. mp=74-76° C. $^1$H NMR (300 MHz, CDCl$_3$) δ 7.39 (t, J=1.2 Hz, 2H), δ 7.18 (m, 3H), δ 5.36 (d, J=2.7 Hz, 1H), δ 4.83 (s, 1H), δ 4.48 (m, 1H), δ 3.39 (d, J=4.5 Hz, 2H), δ 2.33 (m, 2H), δ 2.02-1.82 (m, 5H), δ 1.55-1.33 (m, 18H), δ 1.12-1.03 (m, 7H), δ 0.96-0.86 (m, 9H), δ 0.67 (s, 3H) ppm; $^{13}$C NMR (75 MHz, CDCl$_3$) δ 156.36, 140.1, 129.1, 129.0, 128.8, 128.7, 126.7, 122.7, 56.0, 56.5, 50.3, 42.6, 42.4, 40.0, 39.8, 38.9, 37.3, 36.8, 36.5, 36.1, 32.2, 32.1, 28.5, 28.5, 28.3, 24.6, 23.2, 22.9, 21.3, 10.6, 10.0, 12.1 ppm; IR $v_{max}$ (cm$^{-1}$) 3419, 2944, 2867, 2089, 1694, 1255, 1137; HRMS (ESI) calcd for $C_{36}H_{55}NO_2$ (M+) 556.4125. found 556.4128.

radecahydro-1H-cyclopenta[a]phenanthren-3-yl 3,4-dihydroquinoline-1(2H)-carboxylate (7f): White solid. mp=107-110° C. $^1$H NMR (300 MHz, CDCl$_3$) δ 7.71 (d, J=8.1 Hz, 1H), δ 7.18 (t, J=7.5 Hz, 1H), δ 7.09 (d, J=7.2 Hz, 1H), δ 6.99 (t, J=7.5 Hz, 1H), δ 5.41 (d, J=4.21 Hz, 1H), δ 4.65 (m,

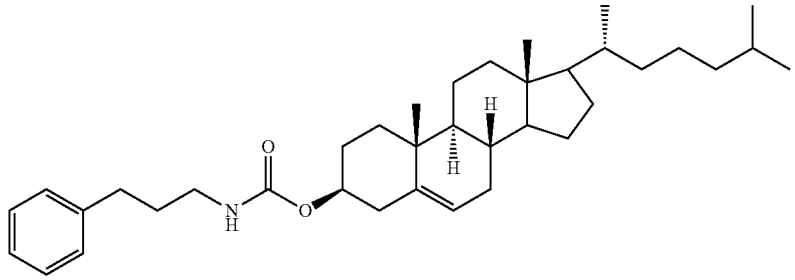

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-phenylpropylcarbamate (4f): White solid. mp=87-89° C. $^1$H NMR (300 MHz, CDCl$_3$) δ 7.24 (t, J=3.3 Hz, 2H), δ 7.25 (t, J=5.4 Hz, 3H), δ 5.35 (d, J=3.6 Hz, 1H), δ 4.89 (t, J=4.5 Hz, 1H), δ 4.49 (m, 1H), δ 3.17 (d, J=4.8 Hz, 2H), δ 2.35 (m, 2H), δ 2.01-1.78 (m, 8H), δ 1.55=1.41 (m, 11H), δ 1.29-1.12 (m, 12H), δ 1.05-0.91 (m, 11H), δ 0.67 (s, 3H) ppm; $^{13}$C NMR (75 MHz, CDCl$_3$) δ 156.5, 141.7, 140.1, 128.7, 128.6, 126.2, 122.7, 74.4, 56.9, 56.5, 50.3, 42.6, 50.7, 50.0, 39.8, 38.9, 37.3, 36.9, 36.5, 35.1, 33.4, 32.1, 31.9, 28.5, 28.4, 28.3, 24.5, 24.2, 23.2, 22.9, 21.3, 19.6, 19.0, 12.2 ppm; IR $v_{max}$ (cm$^{-1}$) 3419, 2944, 2867, 2089, 1694, 1255, 1137; HRMS (ESI) calcd for $C_{37}H_{57}NO_2$ (M+) 570.4282. found 570.4287.

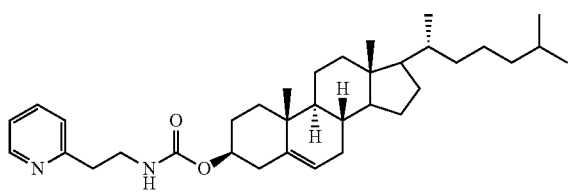

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2-(pyridin-2-yl)ethylcarbamate (pyridin-2-yl)ethylcarbamate (9f). White residue. $^1$H NMR (300 MHz, CDCl$_3$) δ 8.50 (d, J=3.6 Hz, 1H), δ 7.59 (t, 0.9 Hz, 1H), δ 5.7 (d, J=5.7 Hz, 1H), δ 7.09 (t, J=5.7 Hz, 1H), δ 5.73 (s, 1H), δ 5.35 (s, 1H), δ 4.49 (s, 1H), δ 3.58 (d, J=4.2 Hz, 2H), δ 2.99 (t, J=4.8 Hz, 2H), δ 2.34 (m, 2H), δ 2.02-1.81 (m, 5H), δ 1.54-1.34 (m, 10H), δ 1.19-1.08 (m, 11H), δ 1.06-0.86 (m, 14H), δ 0.68 (s, 3H) ppm; $^{13}$C NMR (75 MHz, CDCl$_3$) δ 159.6, 156.3, 149.4, 140.0, 136.6, 123.6, 122.5, 121.6, 74.2, 56.9, 56.4, 50.2, 42.5, 40.4, 39.9, 39.7, 38.8, 37.0, 36.7, 36.4, 32.1, 32.0, 28.4, 28.4, 28.2, 24.5, 24.1, 23.0, 22.8, 21.2, 19.5, 18.9, 12.1 ppm; IR $v_{max}$ (cm$^{-1}$) 3434, 2938, 2869, 2094, 1708, 1641, 1264; HRMS (ESI) calcd for $C_{35}H_{54}N_2O_2$ (M+) 535.4259. found 535.4257.

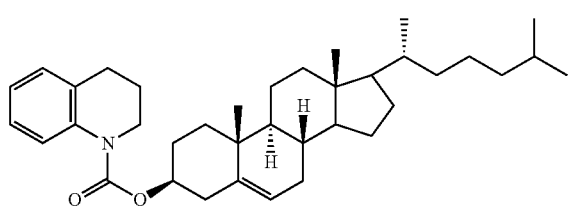

(3 S, 8 S, 9 S, 10R, 13R)-10,13-dimethyl-17-((R)-6-methylheptan-2-yl)-2,3,4,7,8,9,10,11,12,13,14,15,16,17-tet- 1H), δ 3.76 (t, J=5.7 Hz, 2H), δ 2.77 (t, J=6.6 Hz, 2H), δ 2.45 (m, 2H), δ 2.04-1.89 (m, 7H), δ 1.86-1.55 (m, 8H), δ 1.44-1.15 (m, 10H), δ 1.12-1.04 (m, 9H), δ 0.94-0.88 (m, 9H), δ 0.69 (s, 3H), $^{13}$C NMR (75 MHz, CDCl$_3$) δ 154.6, 140.0, 138.6, 130.1, 128.8, 126.1, 124.2, 123.6, 122.8, 75.9, 56.9, 56.4, 40.3, 44.9, 42.6, 39.9, 39.8, 38.8, 37.3, 36.9, 36.4, 36.1, 32.2, 32.1, 28.5, 28.4, 28.3, 27.7, 24.5, 24.1, 23.7, 23.1, 22.1, 21.3, 19.5, 18.9, 12.1 ppm; IR $v_{max}$ (cm$^{-1}$) 3408, 2962, 2927, 1717, 1620, 1602, 1457; HRMS (ESI) calcd for $C_{37}H_{55}NO_2$ (M+) 568.4125. found 568.4127.

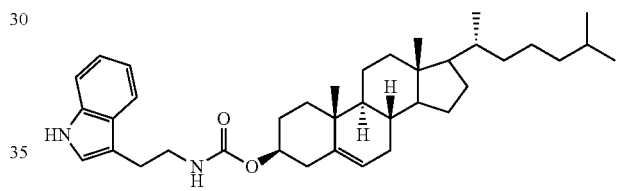

(3 S, 8 S, 9 S, 10R, 13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2-(1H-indol-3-yl)ethylcarbamate (10f): Light yellow solid. mp=149-152° C. $^1$H NMR (300 MHz, CDCl$_3$) δ 8.57 (s, 1H), δ 7.54 (d, J=7.2 Hz, 1H), δ 7.26 (d, J=7.2 Hz, 1H), δ 7.10 (m, 2H), δ 6.79 (s, 1H), δ 5.31 (s, 1H), δ 4.90 (s, 1H), δ 4.52 (s, 1H), δ 3.41 (s, 2H), δ 2.87 (s, 2H, δ 2.27 (s, 2H), δ 1.99-1.77 (m, 5H), δ 1.52-1.34 (m, 11H), δ 1.12-0.88 (m, 22H), δ 0.66 (s, 3H) ppm; $^{13}$C, NMR (75 MHz, CDCl$_3$) δ 156.8, 140.0, 136.8, 127.6, 122.9, 122.6, 122.2, 119.5, 118.9, 112.8, 111.8, 74.7, 56.9, 56.5, 50.3, 42.6, 41.7, 40.1, 39.9, 38.9, 37.3, 36.8, 36.5, 36.2, 32.2, 28.6, 28.4, 24.7, 23.3, 22.9, 21.4, 19.7, 19.2, 12.2 ppm; IR $v_{max}$ (cm$^{-1}$) 3412, 3056, 2945, 2868, 2247, 1697, 1515; HRMS (ESI) calcd for $C_{36}H_{54}N_2O_2$, (M+) 547.4259. found 547.4257.

Example 2: Activity Testing

Standard assays are employed to assess the effect of the aryl carbamate compounds on the formation, inhibition and/or dispersion of bacterial biofilms, or other microorganisms (e.g., fungi), that are infective to plants.

For example, plant-infective bacteria are allowed to form biofilms in a multi-well plate in the absence or presence of one or more compounds. Planktonic (or free growing) bacteria are then removed, wells washed vigorously, and crystal violet added. Crystal violet stains the remaining bacteria which, following ethanol solubilization, is quantitated by spectrophotometry ($A_{540}$). Time-dependent and concentration-dependent analyses of the inhibition and/or dispersion activity of each compound are performed.

Field testing may also be performed.

The foregoing is illustrative, and is not to be construed as limiting thereof. The invention is defined by the following claims, with equivalents of the claims to be included therein.

That which is claimed is:

1. A method of removing or inhibiting bacterial biofilm formation or bacterial infection in a plant or plant part thereof, comprising applying to said plant or plant part a treatment effective amount of a compound of Formula (I):

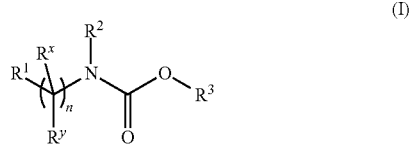

wherein:
R$^1$ is an aryl, an amine-substituted aryl, or a heteroaryl having at least one nitrogen atom;
n=0 to 10, saturated or unsaturated;
each occurrence of R$^x$ and R$^y$ is present or absent (depending upon chain saturation), and is each independently H or alkyl;
R$^2$ is selected from the group consisting of: H, alkyl, alkenyl and alkynyl; and
R$^3$ is alkyl, substituted cycloalkyl or unsubstituted cycloalkyl,
or an agriculturally acceptable salt thereof.

2. The method of claim 1, wherein said plant is a fruit crop plant or a vegetable crop plant.

3. The method of claim 1, wherein said plant is a turfgrass or ornamental plant.

4. The method of claim 1, wherein said bacterial biofilm formation or bacterial infection is citrus canker.

5. The method of claim 1, wherein said plant is a citrus tree.

6. The method of claim 1, wherein R$^1$ is phenyl.

7. The method of claim 1, wherein n=1 to 5.

8. The method of claim 1, wherein R$^3$ is alkyl.

9. The method of claim 1, wherein said compound is ethyl-N-(2-phenethyl) carbamate, or an agriculturally acceptable salt thereof.

10. A method of removing or inhibiting bacterial biofilm formation or bacterial infection in a plant or plant part thereof, comprising applying to said plant or plant part a treatment effective amount of a compound of Formula (I):

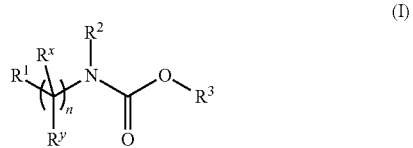

wherein:
R$^1$ is an aryl, an amine-substituted aryl, or a heteroaryl having at least one nitrogen atom;
n=0 to 10, saturated or unsaturated;
each occurrence of R$^x$ and R$^y$ is present or absent (depending upon chain saturation), and is each independently H or alkyl;
R$^2$ is selected from the group consisting of: H, alkyl, alkenyl and alkynyl; and
R$^3$ is alkyl, substituted cycloalkyl or unsubstituted cycloalkyl,
or an agriculturally acceptable salt thereof,
in combination with a microbicide.

11. The method of claim 10, wherein said microbicide comprises copper.

12. The method of claim 10, wherein said microbicide comprises copper hydroxide.

13. The method of claim 10, wherein said microbicide is an antibiotic or a bacteriophage.

14. The method of claim 10, wherein said applying step is carried out by applying said active compound and said microbicide simultaneously.

15. The method of claim 10, wherein said applying step is carried out by applying said active compound and said microbicide sequentially.

16. The method of claim 10, wherein R$^1$ is phenyl.

17. The method of claim 10, wherein n=1 to 5.

18. The method of claim 10, wherein R$^3$ is alkyl.

19. The method of claim 10, wherein said compound is ethyl-N-(2-phenethyl) carbamate, or an agriculturally acceptable salt thereof.

20. The method of claim 1, wherein said bacterial biofilm formation or bacterial infection is caused by a *Xanthomonas* species.

21. The method of claim 1, wherein said bacterial biofilm formation or bacterial infection is citrus canker is caused by *Xanthomonas axonopodis*.

22. The method of claim 10, wherein said bacterial biofilm formation or bacterial infection is caused by a *Xanthomonas* species.

23. The method of claim 10, wherein said bacterial biofilm formation or bacterial infection is citrus canker caused by *Xanthomonas axonopodis*.

24. A method of removing or inhibiting citrus canker in a plant or plant part in need thereof, comprising applying to said plant or plant part a treatment effective amount of ethyl-N-(2-phenethyl) carbamate, or an agriculturally acceptable salt thereof.

25. The method of claim 24, wherein the citrus canker is caused by *Xanthomonas axonopodis*.

26. The method of claim 24, wherein said ethyl-N-(2-phenethyl) carbamate, or an agriculturally acceptable salt thereof, is applied in combination with a microbicide.

27. The method of claim 26, wherein said microbicide comprises copper.

28. The method of claim 26, wherein said microbicide is an antibiotic.

29. The method of claim 26, wherein said microbicide is a bacteriophage.

* * * * *